(12) United States Patent
Friedman et al.

(10) Patent No.: US 8,313,440 B2
(45) Date of Patent: Nov. 20, 2012

(54) INFANT BREATH COLLECTOR

(76) Inventors: Mitchell Friedman, Baltimore, MD (US); Stanley J. Konopka, Franklin, TN (US); Shane A. Crabtree, Murfreesboro, TN (US)

( * ) Notice: Subject to any disclaimer, the term of this patent is extended or adjusted under 35 U.S.C. 154(b) by 896 days.

(21) Appl. No.: 12/316,353

(22) Filed: Dec. 11, 2008

(65) Prior Publication Data

US 2009/0187113 A1 Jul. 23, 2009

Related U.S. Application Data

(60) Provisional application No. 61/011,909, filed on Jan. 22, 2008.

(51) Int. Cl.
*A61B 5/08* (2006.01)
(52) U.S. Cl. ........................... 600/543; 600/529
(58) Field of Classification Search .................... None
See application file for complete search history.

(56) References Cited

U.S. PATENT DOCUMENTS

| | | | |
|---|---|---|---|
| 3,395,701 A * | 8/1968 | Bartlett, Jr. et al. | 600/532 |
| 4,190,045 A | 2/1980 | Bartels | |
| 4,487,055 A * | 12/1984 | Wolf | 73/23.3 |
| 5,081,871 A | 1/1992 | Glaser | |
| 5,140,993 A | 8/1992 | Opekun, Jr. et al. | |
| 5,327,901 A | 7/1994 | Delente | |
| 5,467,776 A | 11/1995 | Hamilton | |
| 5,924,995 A * | 7/1999 | Klein et al. | 600/532 |
| 6,283,122 B1 | 9/2001 | Adahan | |
| 6,494,202 B2 | 12/2002 | Farmer | |
| 6,723,056 B1 | 4/2004 | Alving et al. | |
| 2003/0050567 A1 | 3/2003 | Baghdassarian | |
| 2004/0038412 A1 | 2/2004 | Yatscoff et al. | |
| 2005/0177057 A1 * | 8/2005 | Friedman et al. | 600/543 |
| 2006/0058696 A1 | 3/2006 | Hamilton | |
| 2006/0186076 A1 | 8/2006 | Shiloni | |

OTHER PUBLICATIONS

Wikipedia; Duckbill Valve. (2007) retrieved from en.wikipedia.org/w/index.php?title=Duckbill_valve&oldid=158991425; p. 1 of 1.*

* cited by examiner

*Primary Examiner* — Cathy Kingdon Worley
(74) *Attorney, Agent, or Firm* — Ober, Kaler, Grimes & Shriver; Royal W. Craig

(57) ABSTRACT

A breath collection apparatus is provided that includes a facemask to cover the nose and mouth of a patient to direct the breath into a collection bag or collection vial. A valve assembly containing a flexible valve member is provided between the facemask and the collection container to direct a breath sample to the collection container while permitting fresh air to enter the facemask upon inhalation. Between the valve assembly and the collection container is a collection container attachment fitting for engaging the valve assembly with the collection container. The collection container attachment fitting can be a two-piece fitting designed to accommodate a flexible bladder used to accumulate multiple breath samples for subsequent delivery to the collection container.

11 Claims, 20 Drawing Sheets

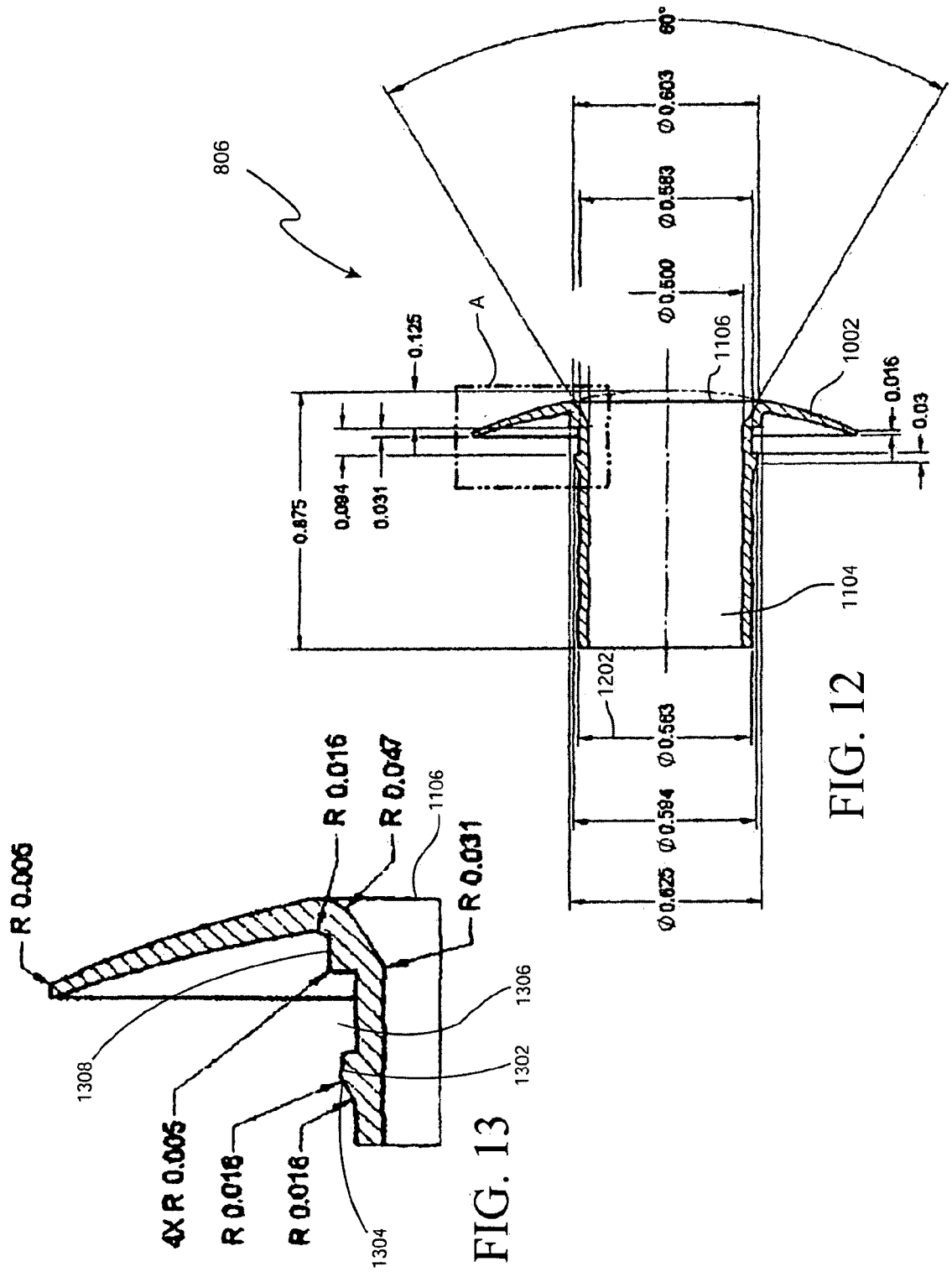

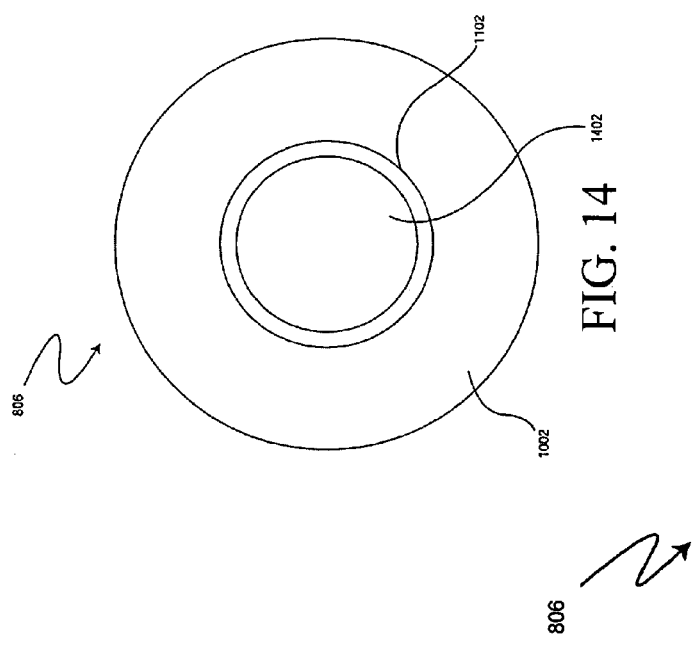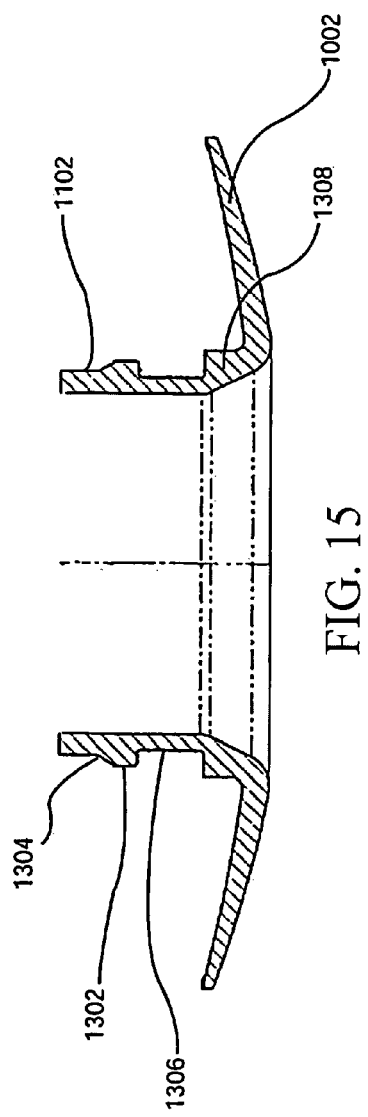

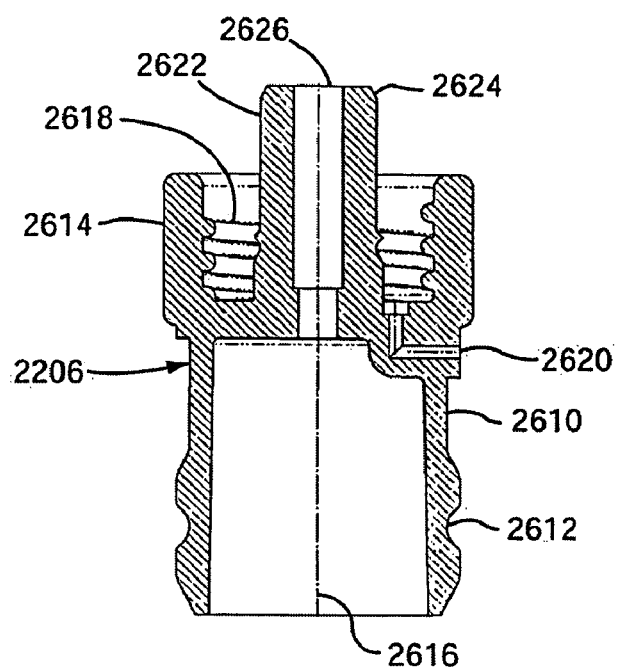
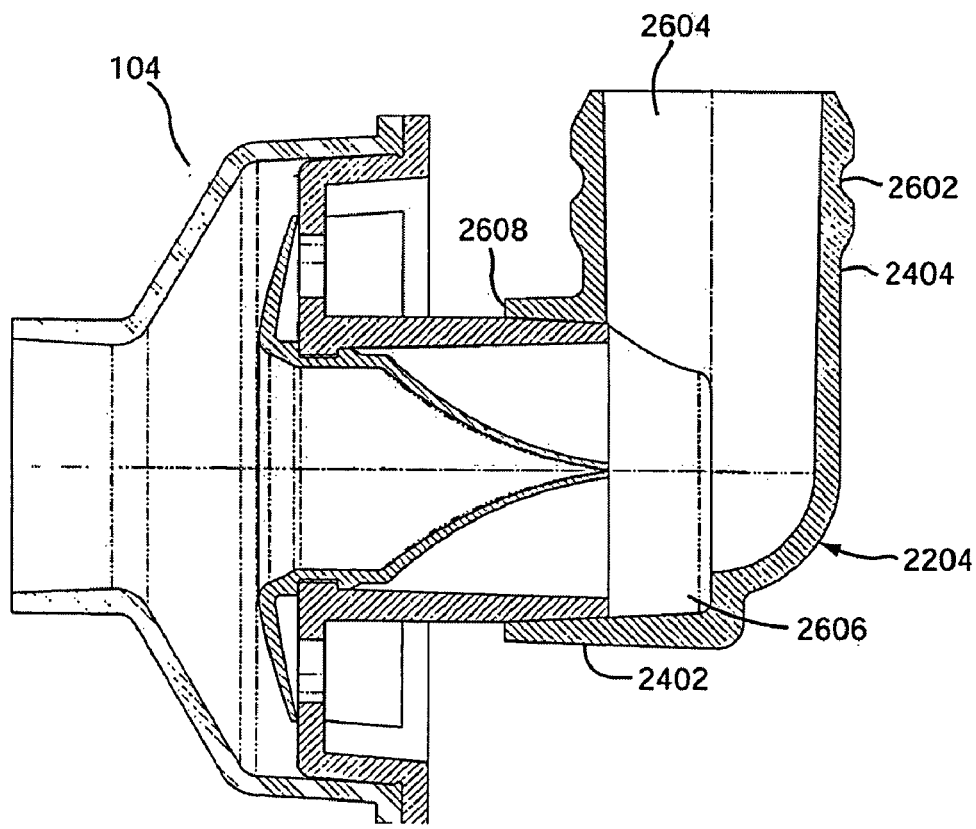
FIG. 26

DETAIL A
SCALE 8:1

INFANT BREATH COLLECTOR

CROSS-REFERENCE TO RELATED APPLICATION

The present application derives priority from provisional application 61/011,909 filed on Jan. 22, 2008, which is incorporated herein by reference.

BACKGROUND OF THE INVENTION

1. Field of the Invention

The present invention relates to breath sampling equipment and in particular to the sampling of air from the lungs of infants.

2. Description of the Background

The constituents of expelled air from a patient's lungs are used for various types of patient diagnoses. To analyze the expelled air, a patient's breath is collected for analysis. A variety of breath collection systems have been developed that generally include a mouthpiece connected to an inlet for inhalation, an outlet for exhalation, and a valve for diverting the exhaled breath into a sampling assembly. These breath collection systems generally use a sampling canister or collection bag to store or transport the breath samples.

For example, U.S. Pat. No. 5,140,993 to Opekun, Jr. et al. issued Aug. 25, 1992, shows a breath collection device that includes a flexible plastic bag having a mouthpiece and inlet valve assembly connected adjacent one end of the bag, and a sample transfer assembly connected adjacent the other end of the bag. A hollow needle penetrates a stopper to permit transfer of a breath sample from the bag to a storage device.

United States Patent Application 20060058696 by Hamilton published Mar. 16, 2006, shows an air sampling apparatus including a bag for containing air and a sensing mechanism coupled to said bag. The self contained sampling and sensing mechanism can be used for visual or other detection of targeted analytes within the breath sample.

United States Patent Application 20030050567 by Baghdassarian published Mar. 13, 2003, shows a device for collecting alveolar breath. A patient exhales a breath into the inlet of a hollow body. The hollow body has two outlets, with a valve disposed in each outlet. The concentration of a specific gaseous component of expired breath is monitored by a gas concentration monitor as the expired breath passes through the hollow body to determine when alveolar breath is present in the hollow body. When alveolar breath is present in the hollow body, the valve in the second outlet is actuated to an open position to collect the alveolar breath in the collection reservoir affixed to the hollow body at the second outlet.

U.S. Pat. No. 5,081,871 to Glaser issued Jan. 21, 1992, shows an apparatus for sampling volumetric quantities of human exhaled breath with three conduits in a "Y" or "T" shaped configuration. The free end of one of the conduits is adapted to connect with the mouth of the subject being tested. Another of the conduits is adapted to pass ambient air to the subject, this conduit being provided with a suitable filtering mechanism, and the third of the three conduits supports an appropriate sampling canister for receiving exhaled breath from the subject. The third conduit is also provided with a one-way check valve.

U.S. Pat. No. 4,190,045 to Bartels issued Feb. 26, 1980, shows a noise reducing exhalation valve and diaphragm for use in exhalation valves of respiratory apparatus to prevent the propagation of harmonic acoustic vibrations. The valve diaphragm employs a cone-shaped central portion.

U.S. Pat. No. 6,723,056 to Alving et al. issued Apr. 20, 2004, shows a device for the collection, storage, or transport of gas samples using a bag with a reagent chamber.

U.S. Pat. No. 6,283,122 to Adahan issued Sep. 4, 2001, shows an exhalation valve for a respirator that includes a hollow flow-through body, an air inlet port, and an air outlet port. The inlet port is connected to a source of compressed air or a respirator, and the air outlet port provides air to a patient. The device also includes an exhalation valve.

United States Patent Application 20040038412 by Yatscoff published Feb. 26, 2004, shows a breath test and kit for the diagnosis of diabetic indications and monitoring glycemic control.

U.S. Pat. No. 5,327,901 to Delente issued Jul. 12, 1994, shows an apparatus for collecting and storing human breath samples including an elongated, hollow container and a breath delivery device for directing a subject's breathe into the container. Self sealing tape is disclosed as a closure means that accommodates the insertion of the breath delivery device into the container and that substantially seals the container.

U.S. Pat. No. 5,467,776 to Hamilton issued Nov. 21, 1995, shows an air sampling device comprising a blow tube connected to a waste air collection bag and an air capture assembly. A person blows a predetermined volume into the blow tube, and after a portion of the air fills the waste bag, a needle pierces a stopper to capture air in a test tube.

In all of the foregoing examples, healthy adults and older children have no problem filling the collection bag, canister, or vial. Infants and other individuals with shallow or weak breathing, however, have difficulties inflating a collection bag, making it difficult for physicians to collect an adequate sample. Very little attention has been directed to this problem.

One example is U.S. Pat. No. 5,924,995 to Klein et al. issued Jul. 20, 1999, which explains how a sample of end-tidal air is collected from a child or infant, and notes that the preferred collection method includes the breath collection device described in U.S. Pat. No. 5,140,993 (above), which includes a resuscitation mask with a one-way inlet valve. The infant's exhaled breath is collected in the collection bag and transferred to an evacuated storage tube, preferably 5 ml in volume. "Older children are capable of blowing directly into the collection bag; or alternatively, they can blow through a straw extending to the bottom of the storage tube when the stopper has been removed. The stopper is replaced after breath collection." Unfortunately, the referenced valve is not designed for an infant, and capturing an adequate sample remains a problem. Moreover, transferring the infant's exhaled breath from the collection bag to an evacuated storage tube is cumbersome, and this process leaves the sample susceptible to contamination.

It would be greatly advantageous to provide an infant breath collector specifically designed for shallow-infant breathing that is both easy for an infant to expel an adequate sample and easy for a physician to collect an adequate sample.

SUMMARY OF THE INVENTION

In accordance with exemplary embodiments of the present invention, an infant breath collector is provided that compensates for shallow-infant breathing. The breath collector includes a facemask that covers both the nose and mouth of the infant and a combination inhalation and exhalation valve coupled to the facemask to permit the inhalation of fresh air through the mask and to direct exhaled air to a collection container, such as a collection bag or collection vial. The combination inhalation and exhalation valve includes an internal diaphragm for admitting fresh air through radial vents and for directing exhaled air centrally out through a conduit to a collection bag. The infant breath collector can also include a polyethylene or similar polymer film bladder coupled between the valve and the collection container using a two-piece attachment fitting. In one embodiment, the attachment fitting is a multi-purpose fitting. The multipurpose fitting includes both a threaded collar for coupling to a vacutainer-type collection vial and a friction or compression fitting extending coaxially outward with the threaded collar for coupling to a breath collection bag such as the Breath Tek™ urea breath test (UBit®) collection bag commercially available from the Meretek Diagnostics group of Otsuka America Pharmaceutical, Inc. of Rockville, Md. Alternatively, the collection container attachment fitting includes either the threaded collar or the compression fitting. In one embodiment, both the collar and fitting are ported. In one embodiment, the collection container attachment fitting is coupled directly to the combination inhalation and exhalation valve.

BRIEF DESCRIPTION OF THE DRAWINGS

FIG. 12 is a cross-section view through line 12-12 of FIG. 10;

FIG. 13 is an enlarged view of section A of FIG. 12;

FIG. 14 is a top view of another embodiment of the flexible valve member with the exhalation valve removed;

FIG. 15 is a cross-section view of the flexible valve member of FIG. 14 with the exhalation valve removed;

FIG. 26 is a cross-section view of the embodiment of a valve assembly and a first and second piece of a two-piece collection container attachment fitting of FIG. 24;

DETAILED DESCRIPTION

Figure 1:
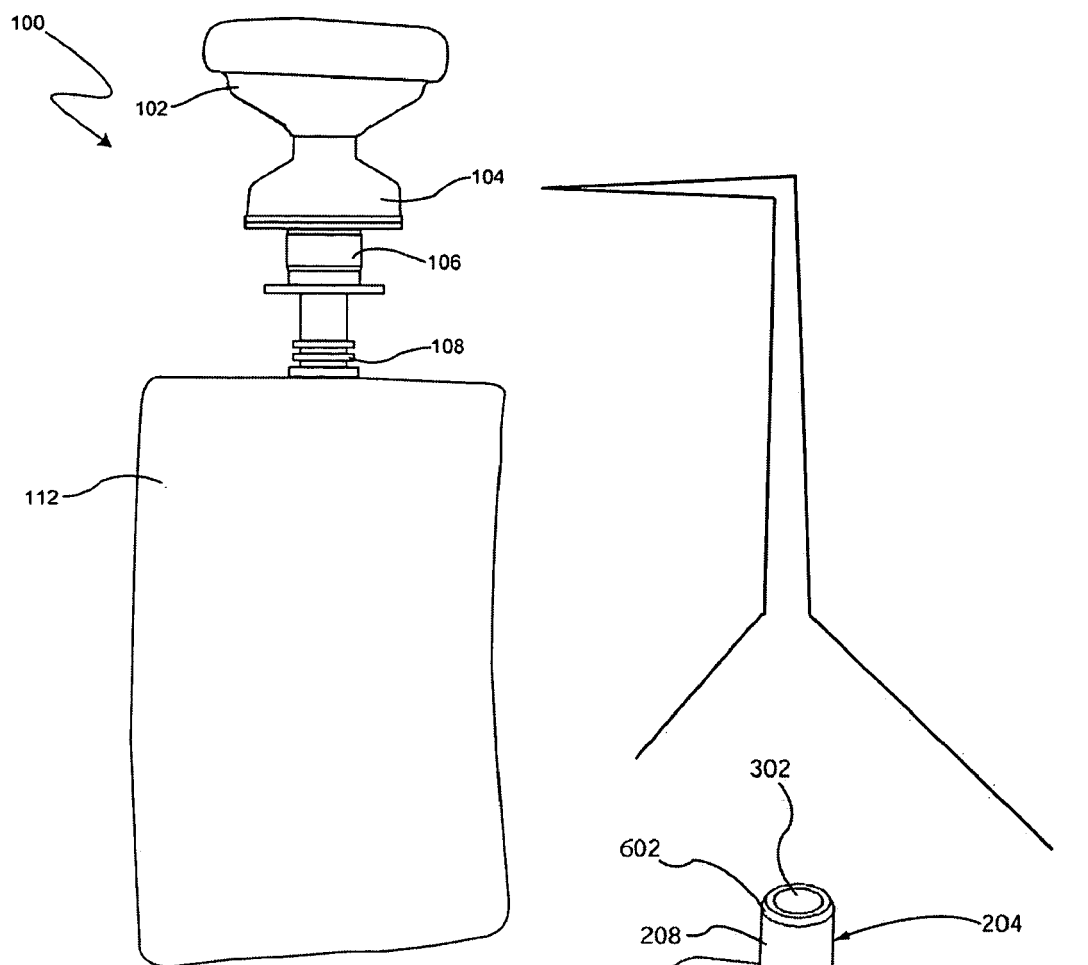
FIG. 1 is a plan view of an embodiment of a breath collection system in accordance with the present invention.

Referring initially to FIG. 1, an exemplary embodiment of a breath collection apparatus 100 in accordance with the present invention is illustrated.

The breath collection apparatus 100 includes a facemask 102 that covers both the mouth and nose of a patient from whom a breath sample is to be collected. The facemask 102 may be sized in accordance with the size or age of the patient, and facemasks of various sizes can be used interchangeably with the breath collection apparatus of the present invention. Suitable arrangements of facemasks are generally known in the art, and the facemask of the present invention includes a rearward coupling for easy attachment to other components of the breath collection apparatus.

Coupled to the facemask 102 is a valve assembly 104 and a collection container attachment fitting 106. Suitable materials for the valve assembly 104 and collection container attachment fitting 106 include plastics, polymers, and elastomers, preferably that can be exposed to sterilization procedures. The valve assembly 104 and attachment fitting 106 are varied depending on the application of the breath collection apparatus, i.e., is it being used with an infant or an adult, and the facemask or collection container being used.

The breath collection apparatus 100 also includes a collection container arranged to accept the breath of the patient. The collection container may be a collection bag 112, as illustrated in FIG. 1, or a collection vial. Suitable bags are known and available in the art and include the Breath Tek™ urea breath test (UBit®) collection bag commercially available from the Meretek Diagnostics group of Otsuka America Pharmaceutical, Inc. of Rockville, Md. The collection bag 112 includes a fill port 108 having a one-way valve (not shown) that allows sample air to be accumulated within the bag, while preventing accumulated air from escaping. Other suitable collection containers may be used.

FIGS. 2-7 collectively illustrate the collection container attachment fitting 106 used for coupling the face mask 102 and valve assembly 104 with the collection bag 112. The collection corwiner attachment fitting 106 includes a valve attachment portion 202, a collection bag attachment portion 204, and a central tab 206 between the other two portions. The valve attachment portion 202 and the collection bag attachment portion 204 are generally cylindrical and coaxially aligned to define the outer boundary of a common air passage through which a sample breath is passed from the valve assembly 104 to the collection bag 112. The collection bag attachment portion 204 has a given diameter for press-fitting into the fill port 108 of a collection bag 112. In one embodiment, the collection bag attachment portion 204 includes a first portion 208 having a first diameter 702 and a second portion 212 disposed between the first portion 208 and the central tab 206, having a second diameter 704. The second diameter 704 is greater than the first diameter 702. In one embodiment, both diameters are selected to fit within the fill port 108 of the collection bag 112. To facilitate the insertion of the collection bag attachment portion 204 into the fill port 108, the first portion 208 includes a beveled or chamfered leading edge 502. Between the first and second portions of the collection bag attachment portion 204 is an annular ridge 210 that defines an annular groove 504 between the annular ridge 210 and the second portion 212. The annular ridge 210 and annular groove 504 are arranged to provide locking engagement with mating structures within the fill port 108. In one embodiment, the annular ridge has a diameter 708 substantially the same and preferably slightly less than the diameter 704 of the second portion 212. In one embodiment, the annular ridge 210 has a cross-sectional angle that is about 90° 712, and the annular groove 504 includes an inclined face 714 leading to the second portion 212 that forms an angle 716 of about 30° with the central axis 714 of the collection bag attachment portion 204. In the illustrated embodiment, the collection bag attachment portion 204 has an overall length 710 of about 0.5 inches.

Figure 3:
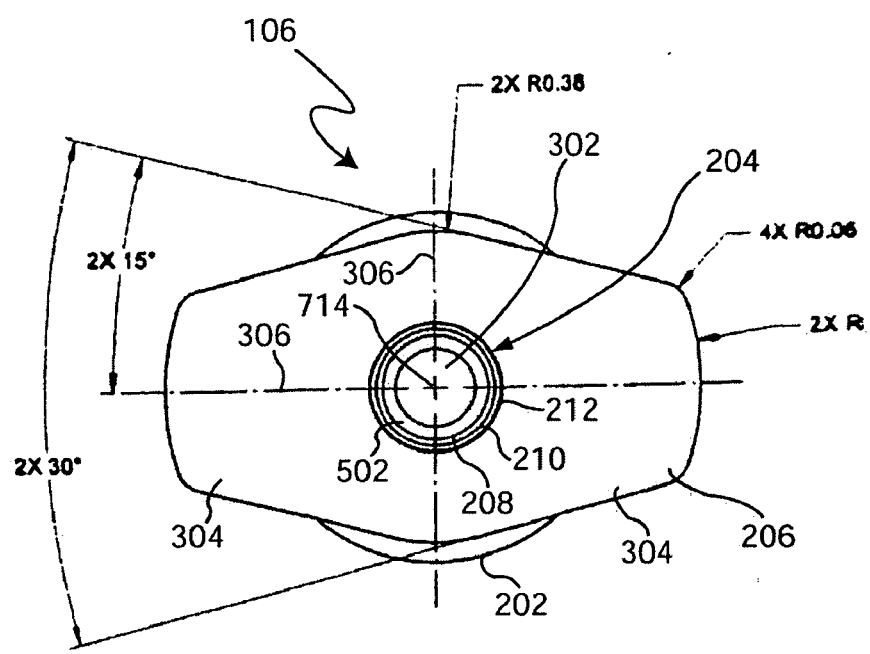
FIG. 3 is a top view of an embodiment of the collection container attachment fitting.
Figure 4:
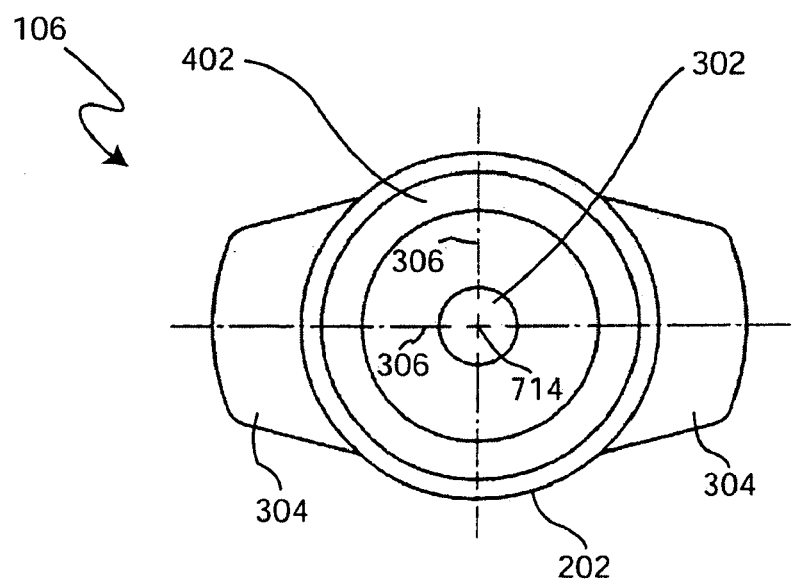
FIG. 4 is a bottom view of the embodiment of the collection container attachment fitting of FIG. 3.
Figure 5:
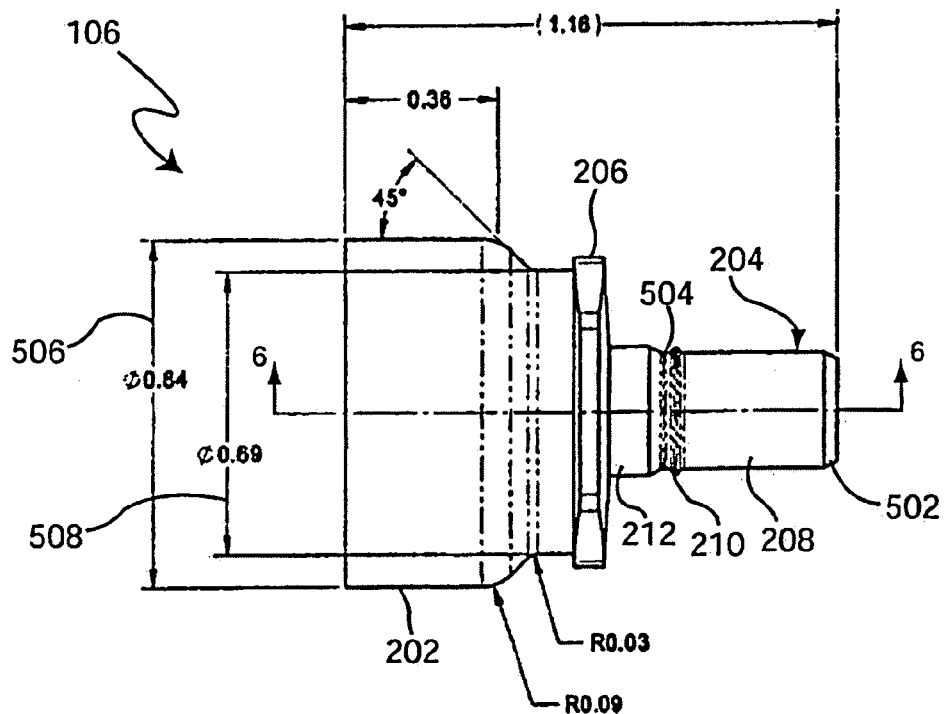
FIG. 5 is a side view of the embodiment of the collection container attachment fitting of FIG. 3.
Figure 6:
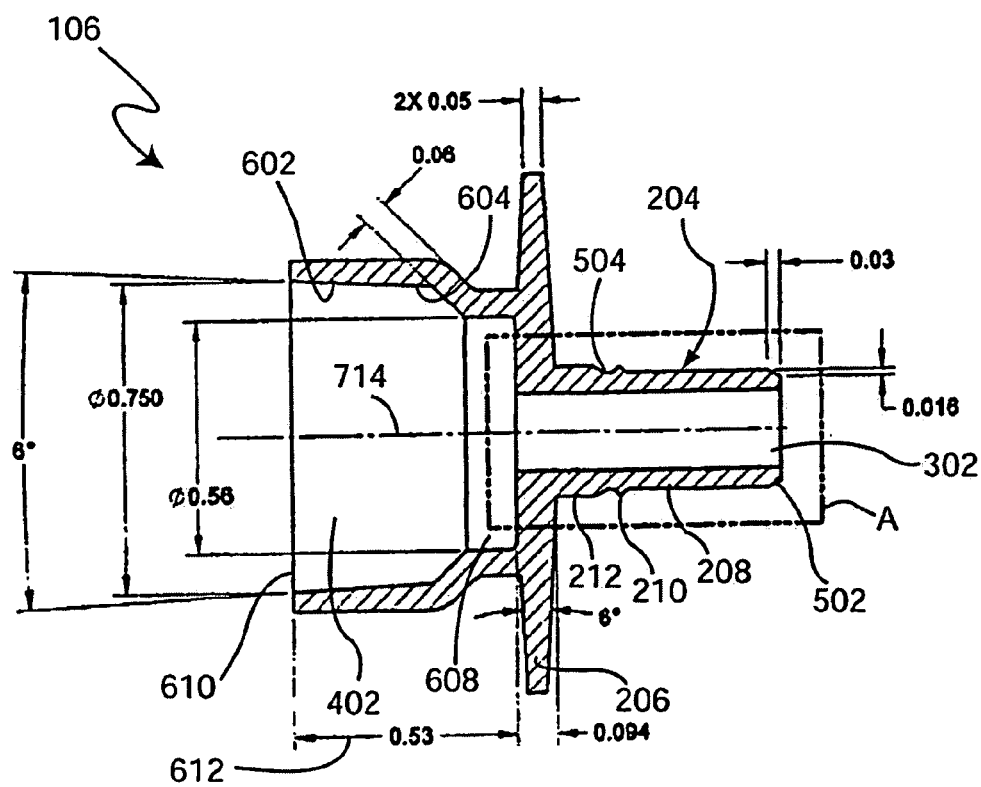
FIG. 6 is a cross-section view through line 6-6 of FIG. 5.
Figure 7:
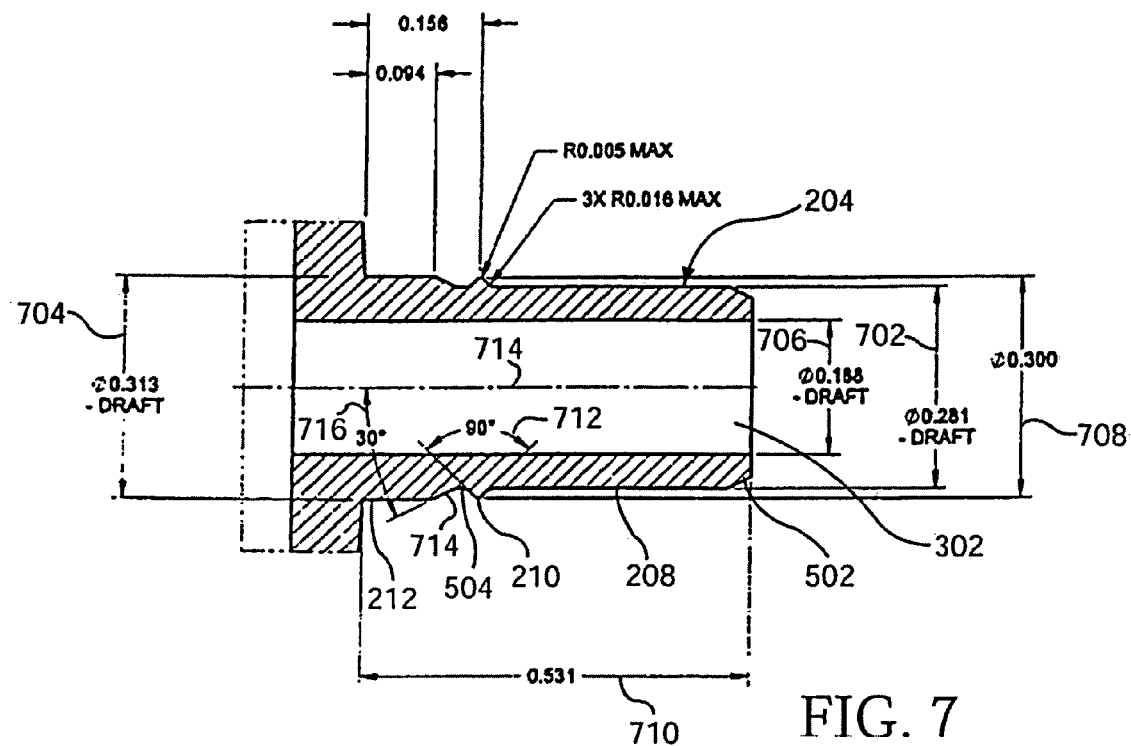
FIG. 7 is an enlarged view of section A of FIG. 6.

As best seen in FIG. 3, the central tab 206 includes two identical tapered portions 304. The tapered portions 304 are symmetrical about both axes of a coordinate system 306 centered along the central axis 714 of the attachment fitting 106. Each tapered portion 304 tapers on all four sides away from the central axis. In general, the central tab 206 is arranged to allow finger placement while removing or seating the attachment fitting 106 with the fill port 108 and the valve assembly 104.

The valve attachment portion 202 is generally cylindrical and has receptacle wall 602, defining an inner cylindrical cavity 402, arranged to be press fit over a corresponding post of the valve assembly 104. In the illustrated embodiment, the valve attachment portion 202 has an outer diameter 506 of about 0.8 to about 0.85 inches and an inner diameter of about 0.69 to about 0.75 inches. In one embodiment, the inner cylindrical cavity 402 has a diameter that decreases from the entrance 610 to the central tab 206. A shoulder 604 is provided that transitions the receptacle wall 602 to an inner portion 608, taking the diameter from about 0.7 inches down to from about 0.5 to about 0.6 inches. The inner cylindrical cavity 402 is in communication with the cylindrical passage 302 that passes through the central tab 206 and the collection bag attachment portion 204. In the illustrated embodiment, the valve attachment portion 202 has an overall length 612 of about 0.5 to about 0.55 inches, approximately the same length as the collection bag attachment portion 204.

Figure 2:
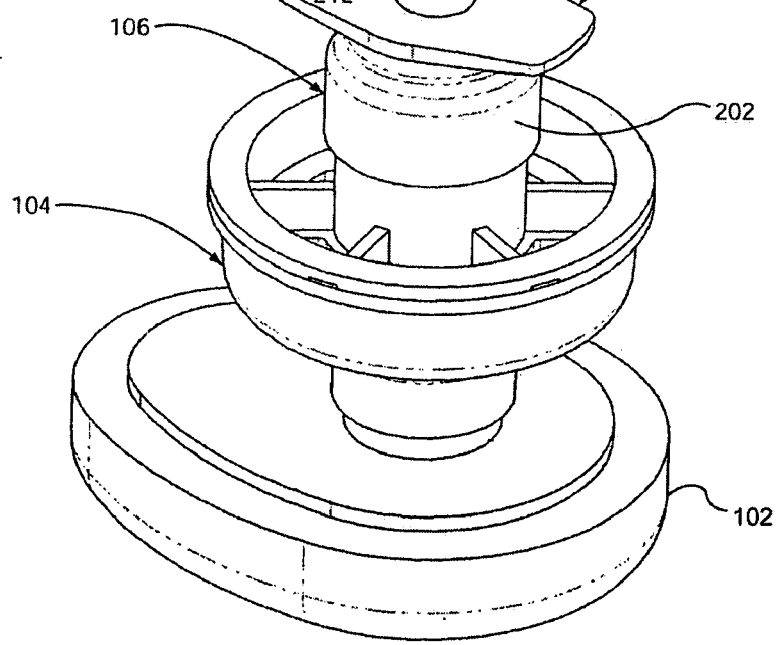
FIG. 2 is a perspective view of an embodiment of a facemask, valve assembly, and collection container attachment fitting.
Figure 8:
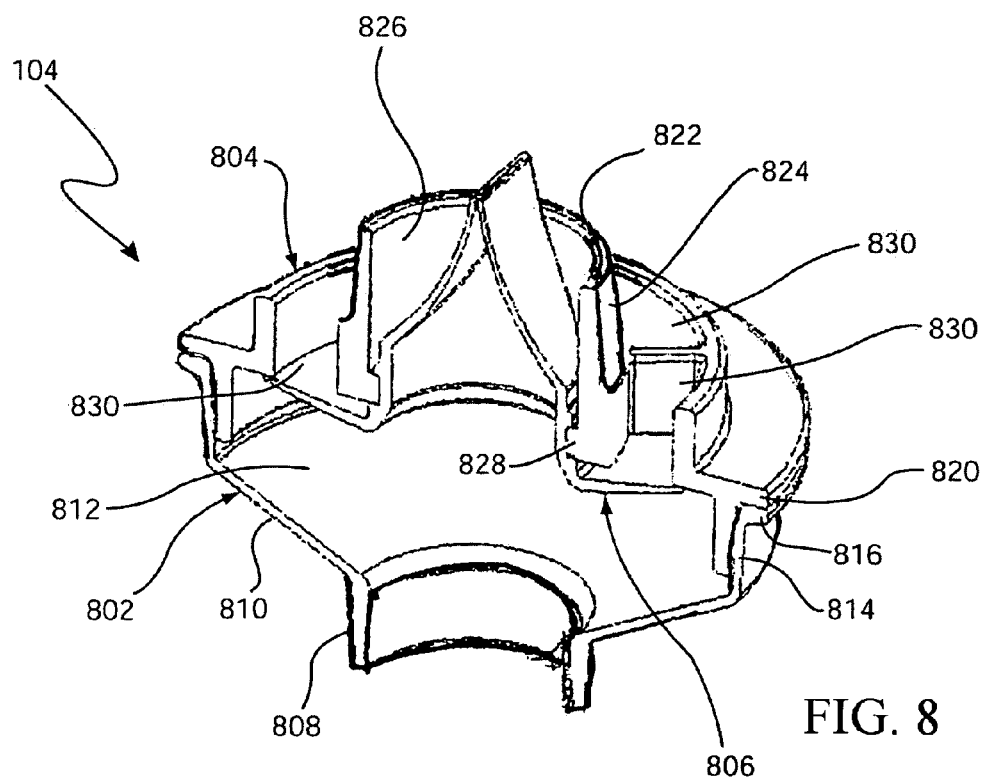
FIG. 8 is a cut-away perspective view of an embodiment of the valve assembly.
Figure 9:
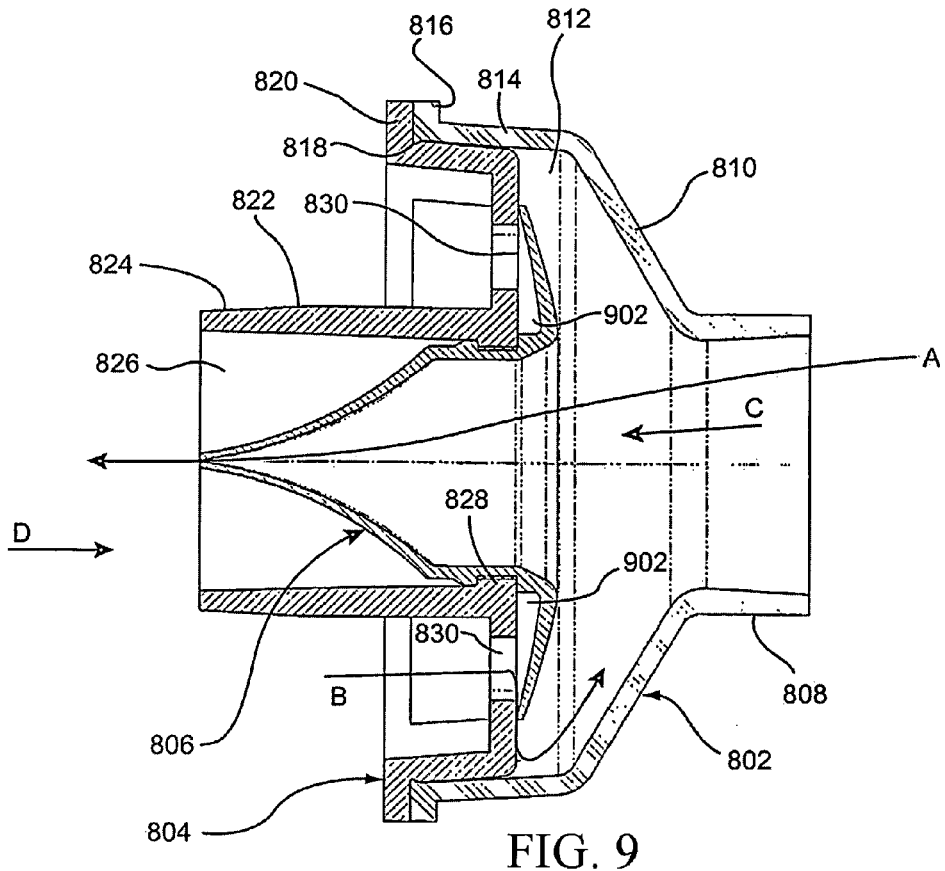
FIG. 9 is a cross-section view of an embodiment of the valve assembly.
Figure 10:
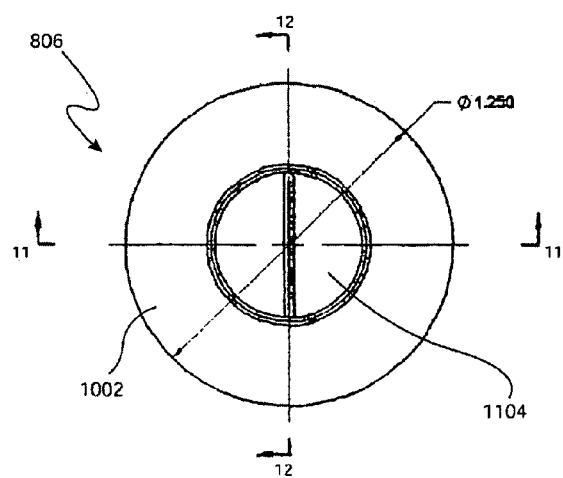
FIG. 10 is a top view of an embodiment of the flexible valve member of the valve assembly.
Figure 11:
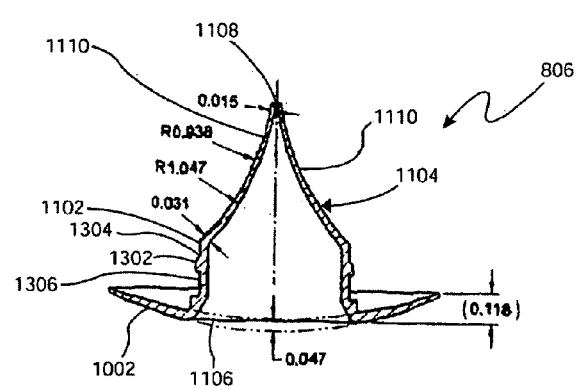
FIG. 11 is a cross-section view through line 11-11 of FIG. 10.
Figure 16:
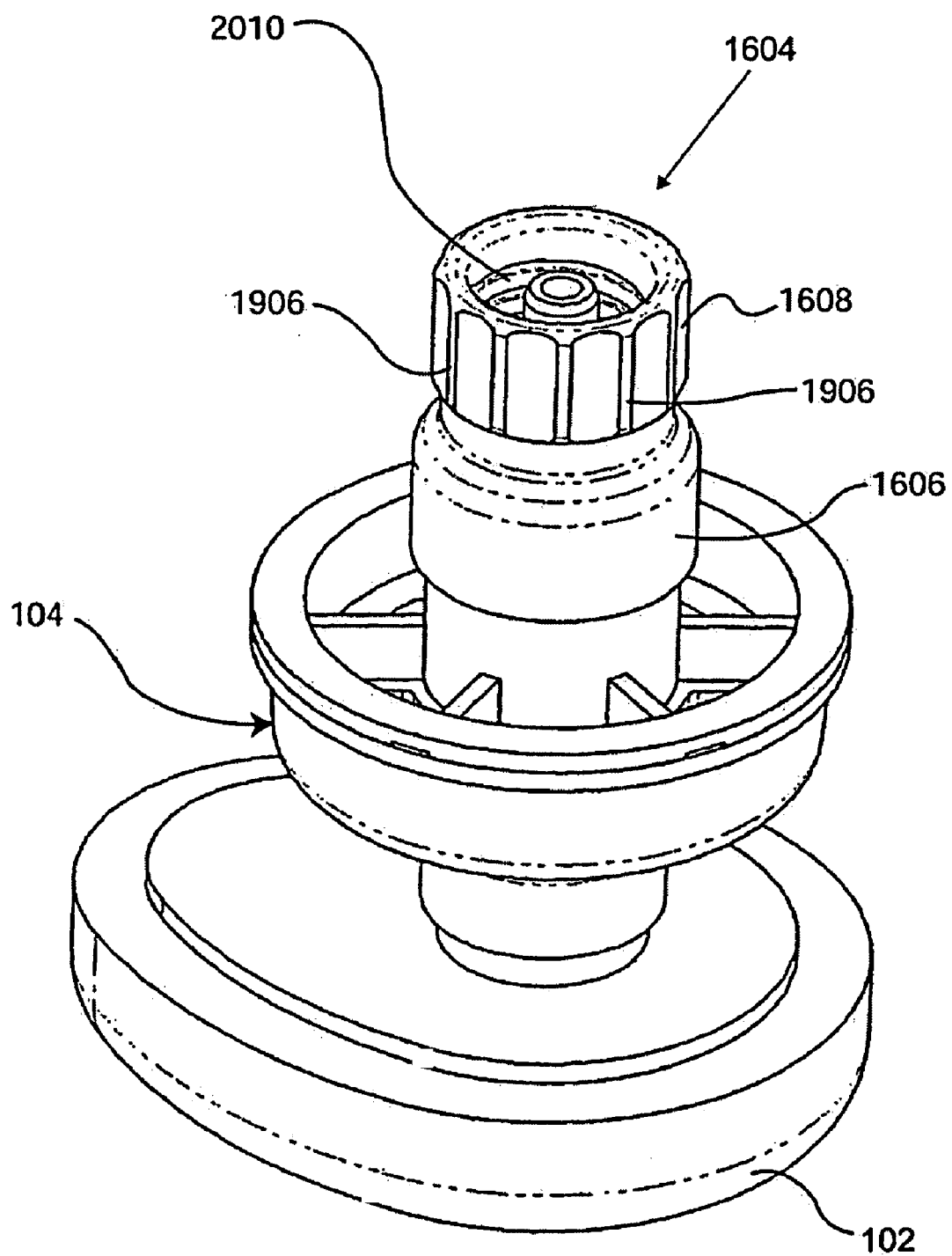
FIG. 16 is a perspective view of another embodiment of a facemask, valve assembly, and collection container attachment fitting for using both collection bags and vials.
Figure 18:
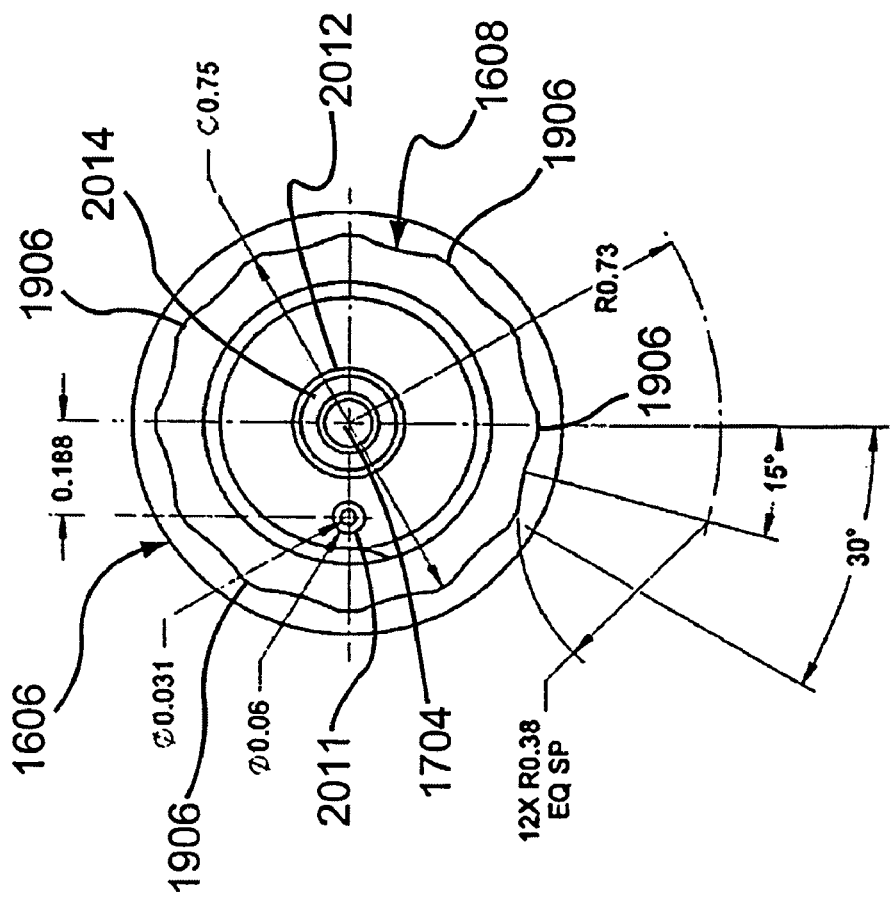
FIG. 18 is a bottom view of the embodiment of the collection container attachment fitting of FIG. 16.
Figure 17:
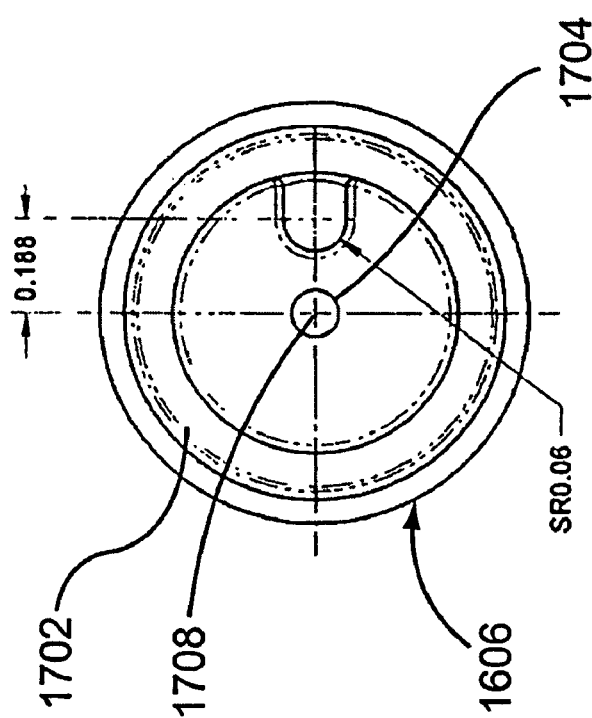
FIG. 17 is a top view of an embodiment of the collection container attachment fitting of FIG. 16.
Figure 19:
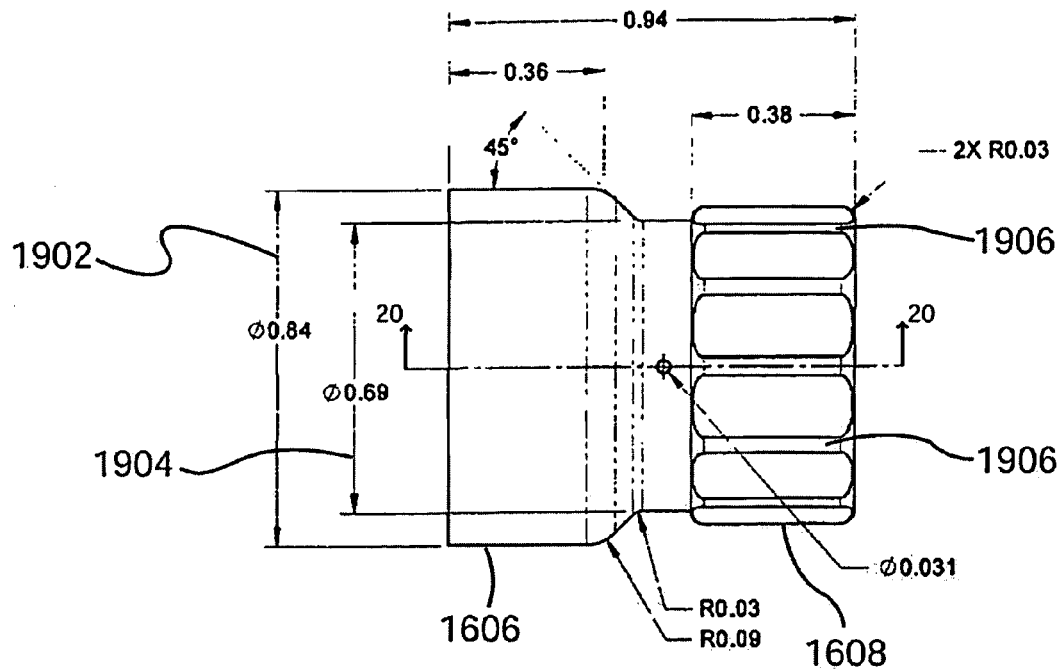
FIG. 19 is a side view of the embodiment of the collection container attachment fitting of FIG. 16.
Figure 20:
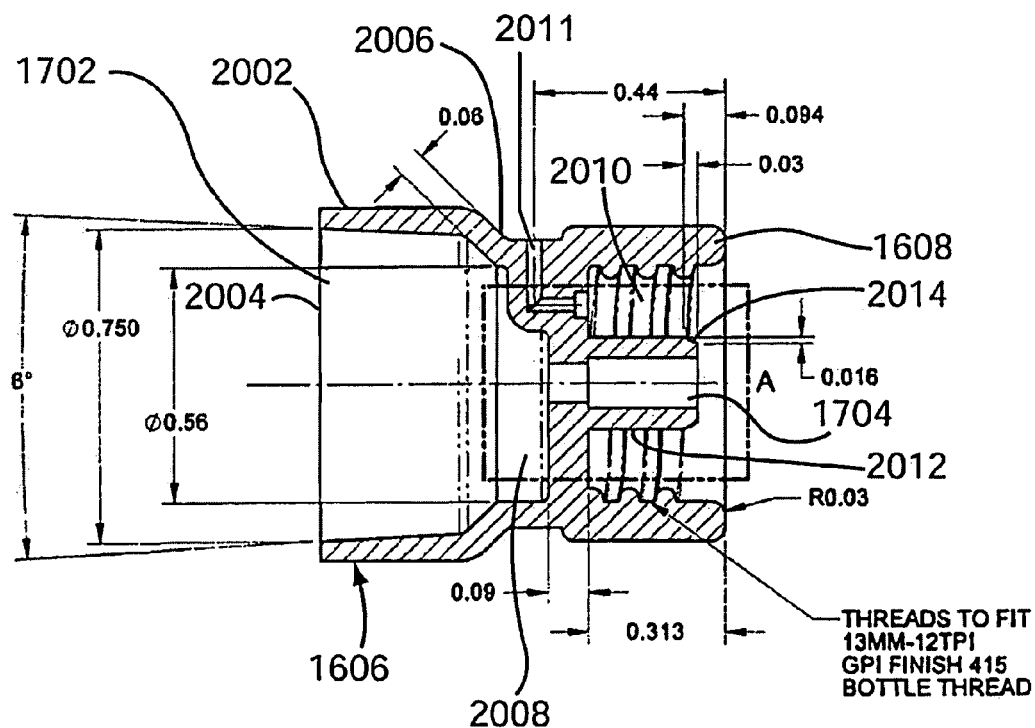
FIG. 20 is a cross-section view through line 20-20 of FIG. 19.
Figure 21:
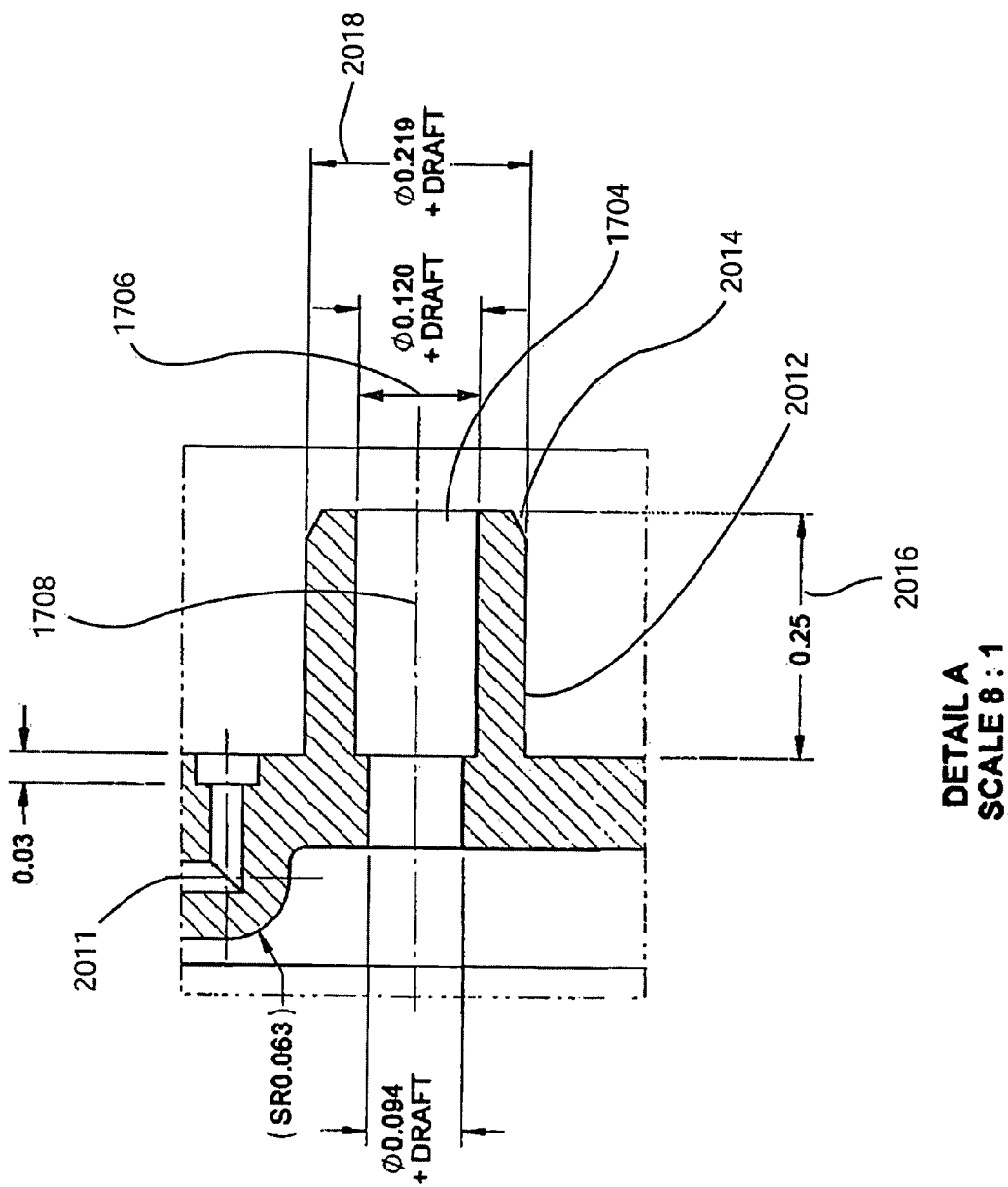
FIG. 21 is an enlarged view of section A of FIG. 20.

FIGS. 2, 8, and 9 illustrate an exemplary embodiment of the valve assembly 104 for use in the breath collection apparatus of the present invention. As illustrated in FIG. 8, the valve assembly 104 is a combination inhalation and exhalation valve comprising an intake housing 802, an outlet housing 804, and a flexible valve member 806. The intake housing 802 connects with the facemask 102, or any other suitable mouthpiece. The intake housing 802 includes an inlet 808 adapted for attachment with the facemask 102. As illustrated, the inlet 808 is cylindrical. In this embodiment, the entire valve assembly 104 is coaxial with the collection container attachment fitting 106. The intake housing 802 flairs out from the inlet 808 to form a housing body 810 that defines a cavity 812 for accepting the outlet housing 804 and the flexible valve member 806. The housing body 810 includes a shoulder portion 814 and a lip 816. The outlet housing 804 fits within the shoulder portion 814 and has a radial flange 820 that contacts the lip 816. Extending from the lip 816 into the cavity 812 is a tang 818 that extends radially around the lip 816 and is arranged to engage a radial groove in the outlet housing 804 adjacent the radial flange 820. The tang 818 and radial groove provide locking engagement of the intake housing 802 and outlet housing 804 while still permitting the two housings to be disengaged for access to the flexible valve member 806.

In one embodiment, the outlet housing 804 includes a cylindrical outlet 822 defining a central cylindrical passage 826. The outlet 822 is sized to accommodate the valve attachment portion 202 of the collection container attachment fitting 106, and in one embodiment, the outlet 822 includes an external taper 824 that corresponds to the taper in the receptacle wall 602 of the valve attachment portion 202. A radial collar 828 extends from outlet 822 into the central cylindrical passage 826. The radial collar 828 has a rectangular cross section. The outlet housing 804 includes a plurality of distinct holes 830 disposed radially around the outlet 822, between the outlet 822 and the radial flange 820. The size and shape of the holes are selected to provide desired air flow for adequate inhalation by the patient. As shown in FIG. 8, the cylindrical outlet 822 does not extend into the cavity 812, and the holes are generally coplanar with the radial flange 820. Alternatively as illustrated in FIG. 9, the cylindrical outlet 822 extends into the cavity 812 and the holes 830 are not coplanar with the radial flange 820. The flexible valve member 806 extends into the central passage 826 while covering the plurality of holes 830.

Referring to FIGS. 10-13, an exemplary embodiment of the valve assembly 104 uses a flexible valve member 806 as illustrated. The valve member 806 preferably is made of silicon rubber and has a wedge or cone with exhalation passage. More specifically, the flexible valve member 806 includes an annular portion 1002 that is cup shaped in cross section and defines the entrance to a central cavity 1106. The annular portion 1002 tapers in thickness from the central cavity 1106 to the edge. The annular portion 1002 is sized to cover the holes 830 in the outlet housing 804. The cup shape biases the annular portion 1002 over the holes 830 (FIG. 9). Extending upward from the inner edge of the annular portion 1002 is a cylindrical neck portion 1102 having a general diameter 1202, which is less than the diameter of the central passage 826 in the area of the radial collar 828, for insertion into the central passage 826. A first protrusion 1302 extends radially around the exterior of the neck portion 1102 to define a radial groove 1306 having a rectangular cross section to accommodate the radial collar 828. Nesting of the radial collar 828 into the radial groove 1306 secures and seals the flexible valve member 806 within the outlet housing 804. The first protrusion 1302 includes a slanted face 1304 to accommodate passage of the first protrusion 1302 over the radial collar 828. In general, the flexible valve member 806 is sufficiently flexible to pass easily over the radial collar 828. A second protrusion 1308 radially extends around the neck portion 1102 on the other side of the radial groove 1306 from first protrusion 1302. In addition to forming one side of the radial groove 1306, the second protrusion 1308 acts as a stop to limit the insertion of the flexible valve member 806 into the central passage 826, which creates an air gap 902 between the center of the annular portion 1002 and the outlet housing 804. In the illustrated embodiment, flexible valve member 806 includes an "umbrella" check valve (the concave annular portion 1002 resembles an open umbrella). The annular portion 1002 flexes towards the outlet housing 804 to create a tight seal over the holes 830 when the pressure on the facemask side of annular portion 1002 exceeds the pressure on the outlet-housing side of the annular portion 1002. This pressure difference occurs during exhalation. The umbrella shape is an improvement over a flat or convex shape that would allow the sealing lip to be forced up and away form the holes 830 rather than sealing tightly.

In one embodiment, coaxially extending from the neck portion 1102 into the central passage 826 is a duck bill portion 1104 having a pair of opposed concave sides 1110 that meet to define an aperture 1108. The concave sides 1110 taper in thickness towards the aperture 1108, and the inwardly concave shape of the sides 1110 biases the aperture 1108 closed. In an alternative embodiment of the flexible valve member 806 illustrated in FIGS. 14 and 15, the duck bill portion 1104 has been eliminated, leaving an open central passage 1402. Otherwise, all of the other components are the same as the previous embodiment. This embodiment should be used with-breath collection bags 112 that contain an inlet check valve, as this check valve prevents the collected breath from being released. This embodiment is more suited to collect breath samples from patients with very shallow or weak breathing.

Returning to FIG. 9 and 11, in operation, breath that is exhaled follows the path indicated by arrow A through the duck bill valve 1104 towards the collection container. The aperture 1108 of the duck bill valve opens under the force of the exhaled breath in the direction of arrow C, which also closes the annular portion 1002 of the flexible valve member 806 over the holes 830. During inhalation, forces in the direction of arrow D hold the aperture 1108 closed, aided by the concave shape of the duck bill sides 1110. Fresh air is drawn into the valve assembly 104 in the direction of arrow B through the holes 830 as the annular portion 1002 lifts away.

FIGS. 16-21 illustrate a breath collection apparatus including a facemask 102, valve assembly 104, and alternative embodiment of the collection container attachment fitting 1604. The valve assembly 104 is as described above. The collection container attachment fitting 1604 is a multi-purpose fitting that includes a valve attachment portion 1606, which is substantially the same as the previously described embodiment of the valve attachment portion 202 of FIG. 2. The collection container attachment fitting 1604 also includes a collection container attachment portion 1608 that is arranged to accommodate a plurality of different collection devices. The illustrated attachment fitting 1604 couples with two different collection containers using a tubular post 2012 for attachment to a collection bag and a threaded collar 2010 for attachment to a collection vial. Although the illustrated attachment fitting 1604 does not include a central tab with extended portions for gripping, a suitable central tab such as the one described above can be included.

In one embodiment, the valve attachment portion 1606 and the collection container attachment portion 1608 are cylindrical and are arranged coaxially to define a common air passage through which the sample breath is passed from the valve assembly 104 to the collection container. The valve attachment portion 1606 has a cylindrical receptacle wall 2002 that defines an inner cylindrical cavity 1702. In the illustrated embodiment, the valve attachment portion 1606 has an outer diameter 1902 of about 0.8 to about 0.85 inches and an inner diameter 1904 of about 0.69 to about 0.75 inches. The cylindrical receptacle wall 2002 is sized to be press fit over a corresponding outlet 822 of the valve assembly 104. In one embodiment, the cylindrical cavity 1702 has a diameter that decreases from the entrance 2004 of the inner cylindrical cavity 1702 towards the collection container attachment portion 1608. A shoulder portion 2006 transitions the receptacle wall 2002 to an inner portion 2008, taking the diameter from about 0.7 inches down to from about 0.5 to about 0.6 inches. The inner cylindrical cavity 1702 and in particular the inner portion 2008 are in communication with a cylindrical passage 1704 that runs through the central, cylindrical post 2012.

The collection container attachment portion 1608 includes an internally threaded collar 2010 that engages with a corresponding threaded end of a collection vial. A plurality of external nubs 1906 assist with connecting the threaded collar 2010 with the threaded portion of a collection vial. In one embodiment, the collection container attachment portion 1608, including the threaded collar 2010, does not spin free of the valve attachment portion 1606, but in another embodiment, the threaded collar 2010 does spin free of the valve attachment portion 1606. Disposed within threaded collar 2010 is a vent 2011 that extends to an exterior surface of the collection container attachment portion 1608. An extension tube 2704 ensures that the "fresh" breath sample arrives at the bottom of vial 2208, thus flushing out any "old" air in the vial 2208 through vent 2011. This flushing action assures a good breath sample. The collection container attachment portion 1608 also includes a central cylindrical post 2012 that can be inserted into the fill port 108 of a collection bag 112 and retained in that position by friction. A beveled or chamfered leading edge 2014 is provided to guide insertion of the post 2012 into the fill port 108. Alternatively, when the attachment fitting 1604 is engaged with a screw-top vial 2208, the cylindrical post 2012 directs breath samples into the vial 2208. In one embodiment, the post has a length 2016 of about 0.25 inches and an external diameter 2018 of from about 0.20 to about 0.22 inches. The central cylindrical post 2012 comprises a central passage 1704.

Figure 22:
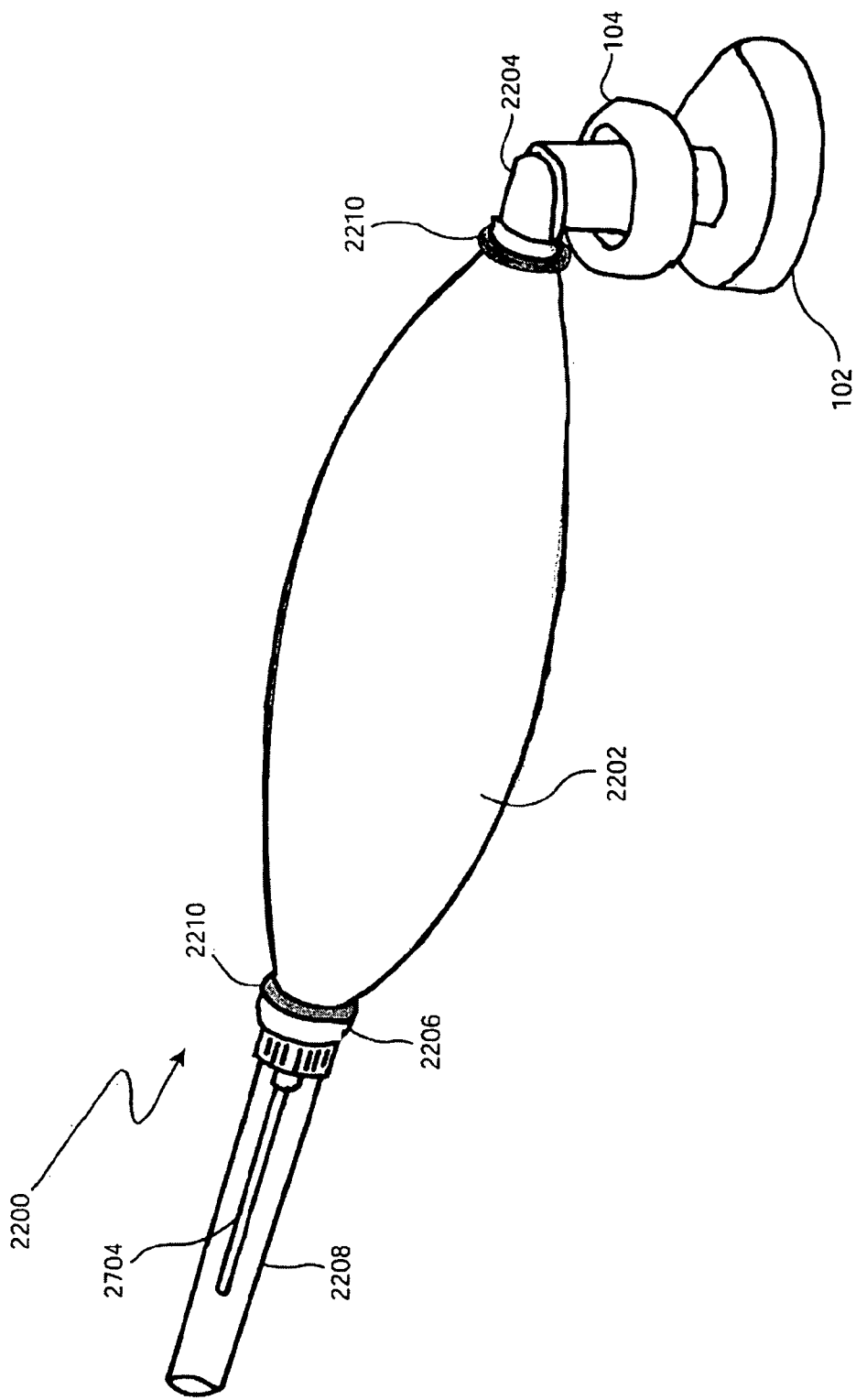
FIG. 22 is a perspective view of another embodiment of the breath collection apparatus of the present invention using a bladder.
Figure 23:
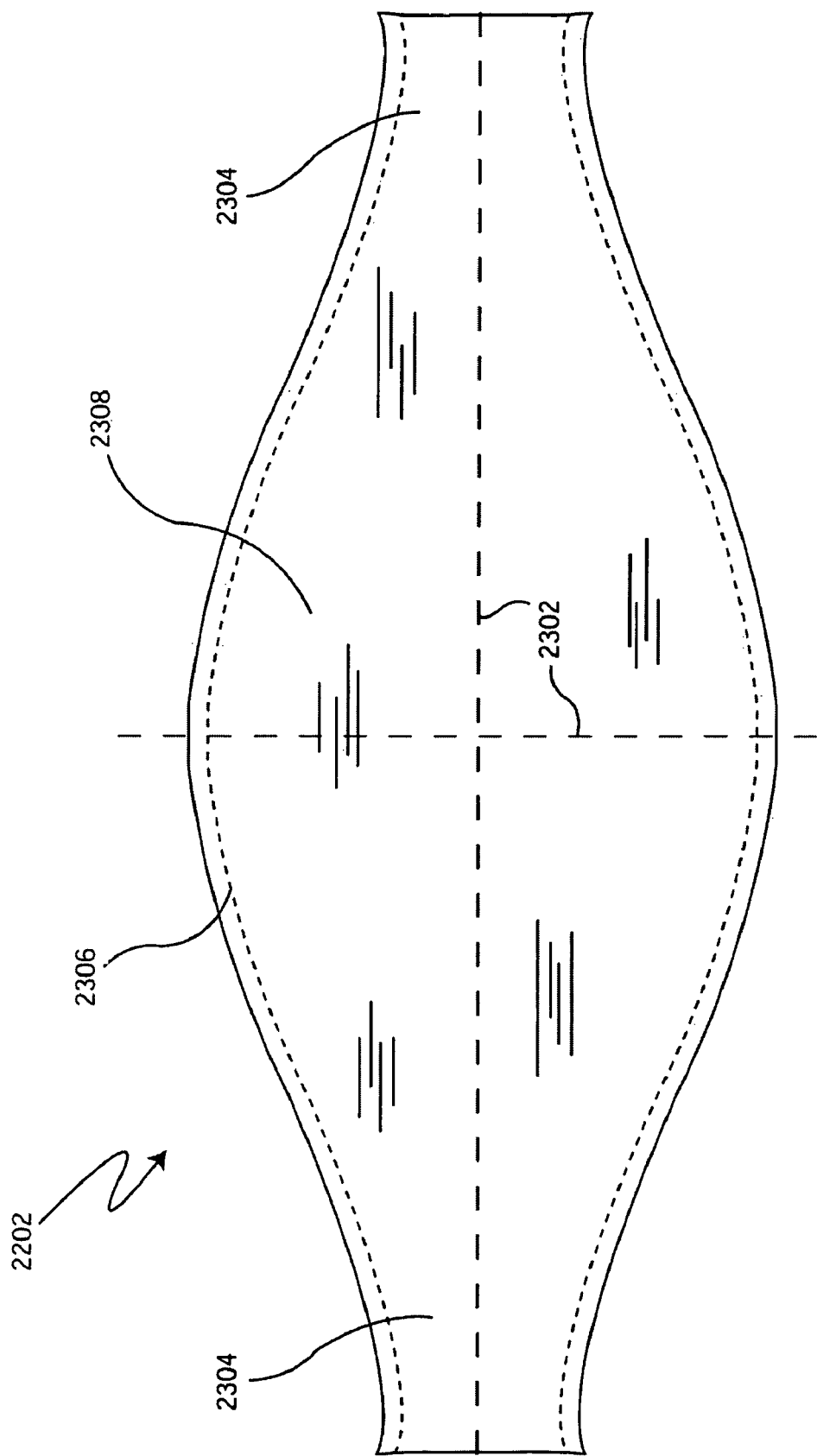
FIG. 23 is a side view of an embodiment of the bladder.

Referring to FIG. 22, in one exemplary embodiment, the breath collection apparatus includes a flexible bladder 2202. In the illustrated embodiment, the bladder is spheroidal and made of a thin and very flexible polymer, preferably a polyethylene film. Referring to FIG. 23, in one embodiment, the bladder 2202 is formed by heat sealing 2306 two identical sheets of flexible material together along the outer edges. The material may be transparent, translucent, or opaque. The bladder 2202 has two open ends 2304 and a central enlarged section 2308 between the two ends 2304. In general, the bladder 2202 is symmetrical about two perpendicular axes 2302. The bladder 2202 allows the person collecting a sample from an infant using a collection vial 2208 to visually confirm that a sufficient volume of breath has been collected. The bladder 2202, being of very thin flexible material, is used to accumulate a breath sample that passes through the valve assembly 104. Following visual confirmation, the bladder 2202 is squeezed or some constricting force is applied to fill the vial 2208 with a good, well-mixed breath sample. The vial 2208 is then quickly removed, and a sealing cap, for example, a threaded cap (not shown), with septum is screwed on, and the vial is transported to a laboratory with a mass spectrometer or other instrument capable of analyzing the breath sample. When the cap is screwed on, the vial 2208 is sealed off so the breath sample cannot escape or become diluted with ambient air.

Figure 24:
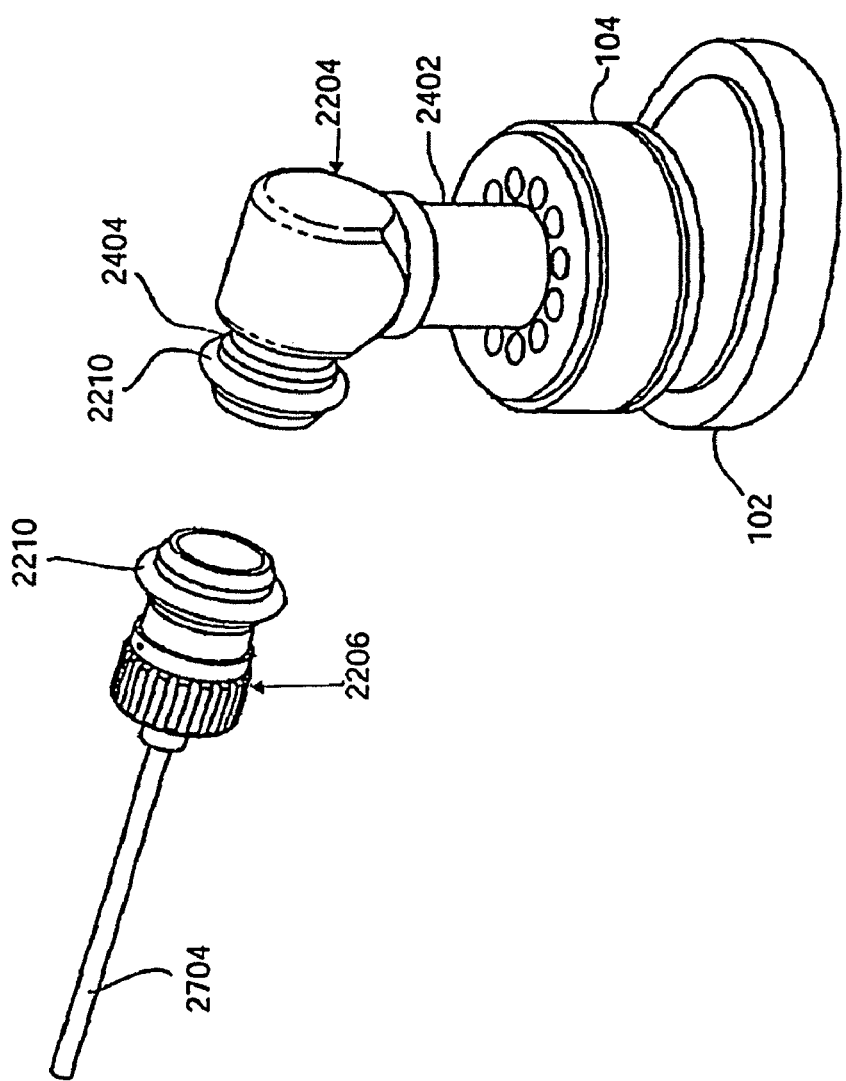
FIG. 24 is perspective view of an embodiment of a facemask, valve assembly, and two-piece collection container attachment fitting.

To accommodate the bladder 2202, the collection container attachment fitting is a two-piece fitting (FIG. 22 and 24). The two-piece fitting includes a first piece 2204, disposed between the valve assembly 104 and the bladder 2202, and a second piece 2206, disposed between the bladder 2202 and the collection vial 2208. In one embodiment, the bladder 2202 is secured to the two-piece collection container attachment fitting by a pair of elastic rings 2210.

Figure 25:
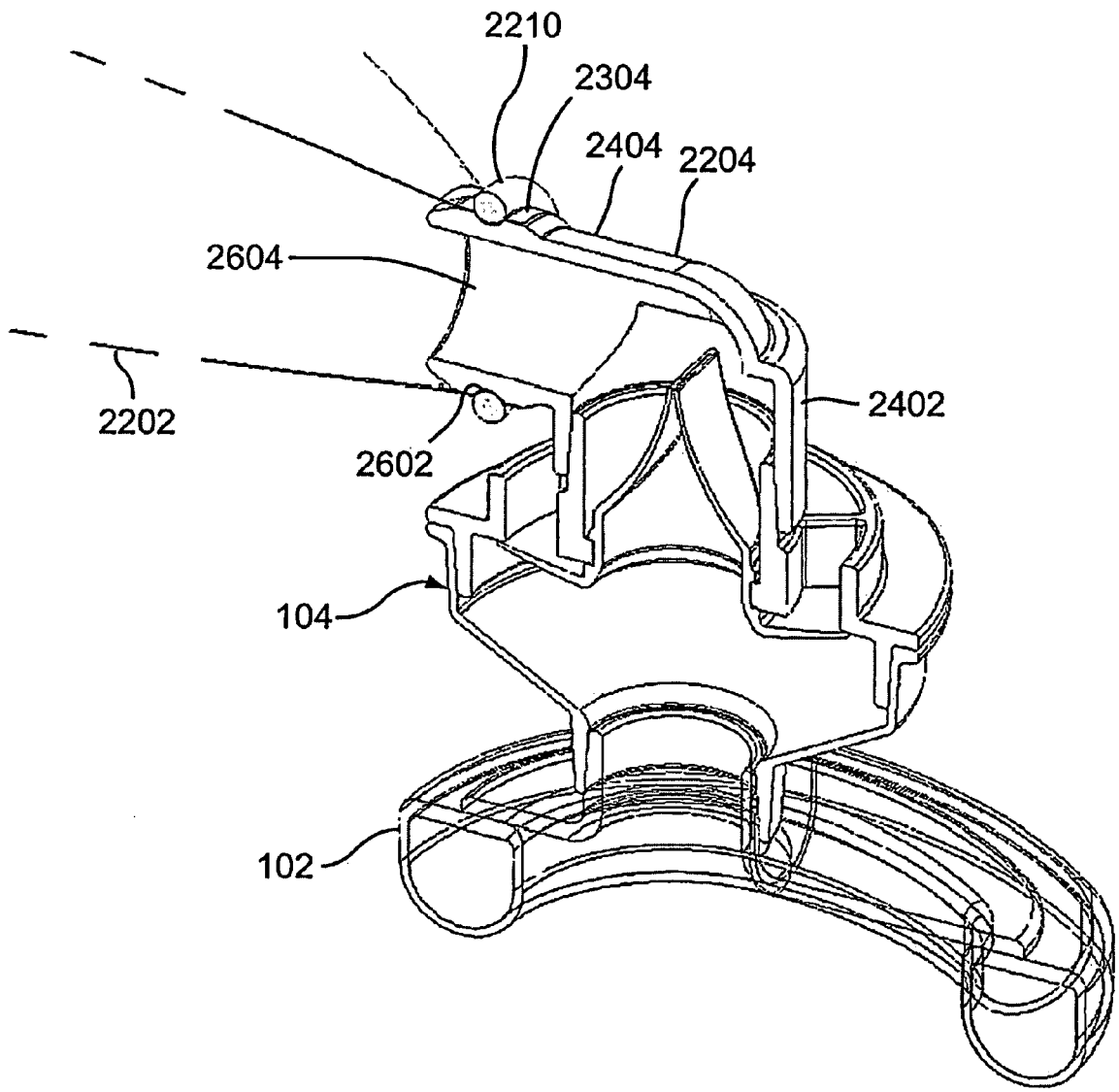
FIG. 25 is a cut-away perspective view of the embodiment of FIG. 24 with bladder attached.

FIGS. 24-26 illustrate exemplary embodiments of the two-piece fitting. In one embodiment, the first piece 2204 includes a valve attachment portion. Suitable arrangements for the valve attachment portion 2402 of the first piece 2204 are the same as described above for the valve attachment portion 202. The valve attachment portion 2402 is cylindrical and defines an inner central cavity 2606. The valve attachment portion 2402 press fits over the outlet 822 of the valve assembly 104. In one embodiment, the valve attachment portion 2402 has an outer diameter of from about 0.8 to about 0.85 inches and an inner diameter of about 0.69 to about 0.75 inches. In another embodiment, the inner cylindrical cavity 2606 has a diameter that decreases from the entrance 2608. The first piece 2204 also includes a bladder attachment portion 2404 extending from the valve attachment portion 2402. The bladder attachment portion 2404 is sized to fit within the open end 2304 of the bladder 2202. The bladder attachment portion 2404 comprises a central passage 2604 that is communication with the cylindrical cavity 2606. Although illustrated with a 90° bend, the first piece 2204 can be straight. In one embodiment, the bladder attachment portion 2404 includes a radial groove 2602 on an exterior surface. The radial groove 2602 is sized to accommodate an elastic ring 2210. In one embodiment, the radial groove 2602 has a generally semi-circular cross section. To attach the bladder 2202, the bladder attachment portion 2404 is inserted into an open end 2304 of the bladder 2202 so that the open end 2304 extends past the radial groove 2602. An elastic ring 2210 is then seated into the radial groove 2602 to seal the bladder 2202 between the elastic ring 2210 and the bladder attachment portion 2404.

Figure 27:
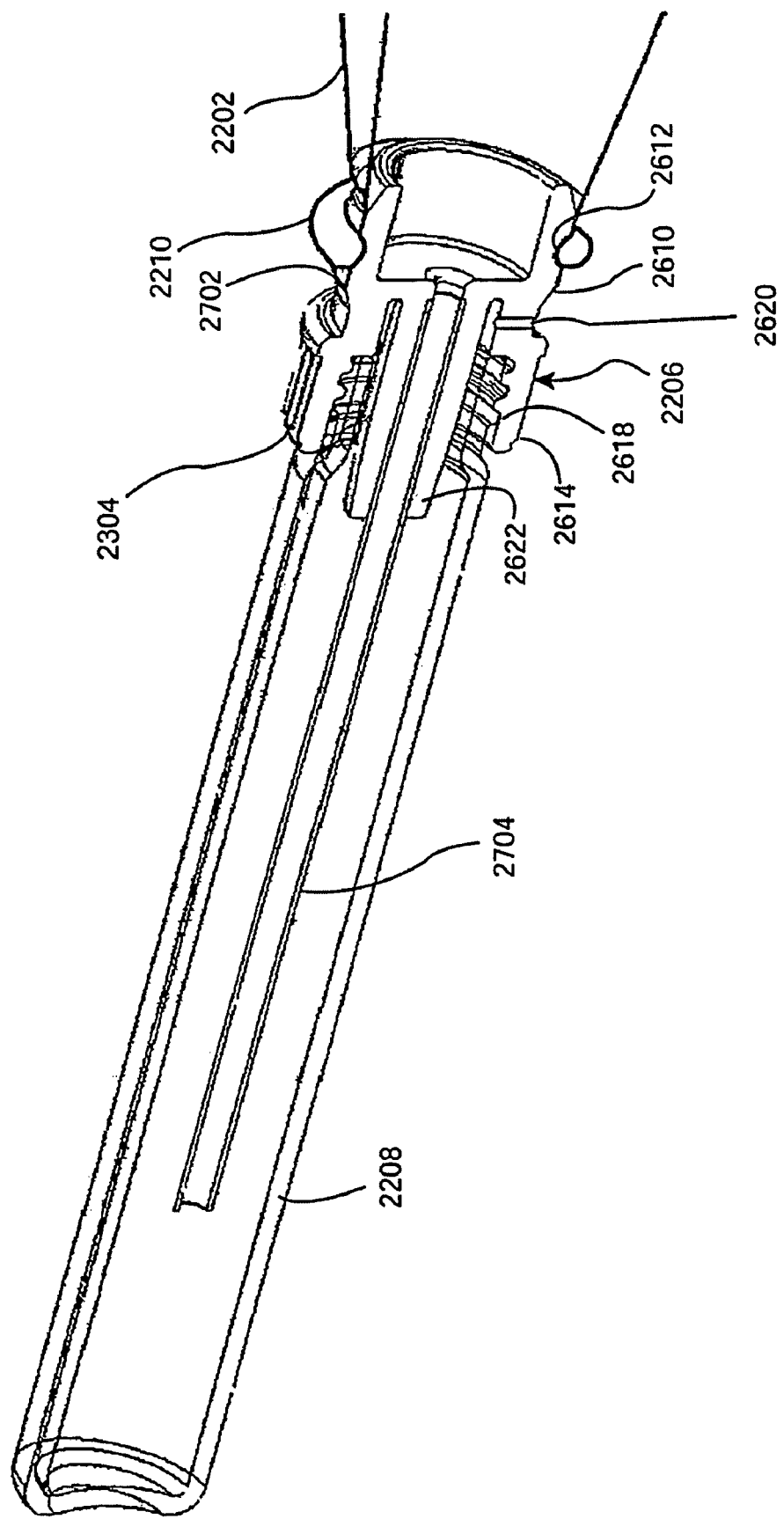
FIG. 27 is a cut-away perspective view of an embodiment of a second piece of a two-piece collection container attachment fitting of FIG. 24 with bladder and collection vial attached.
Figure 29:
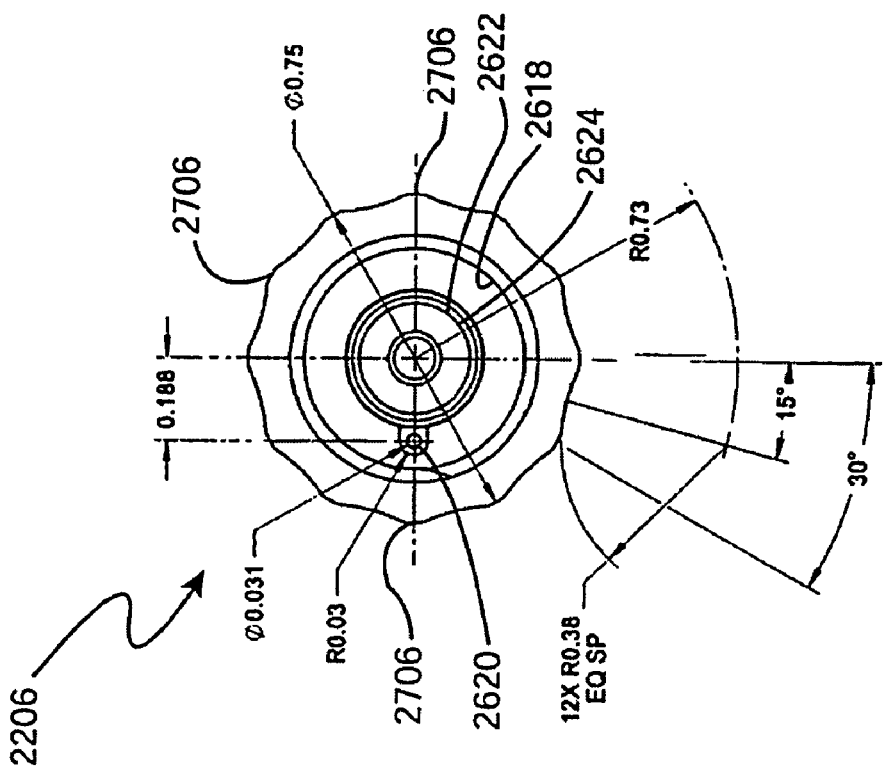
FIG. 29 is a bottom view of the embodiment of a second piece of a two-piece collection container attachment fitting of FIG. 24.
Figure 28:
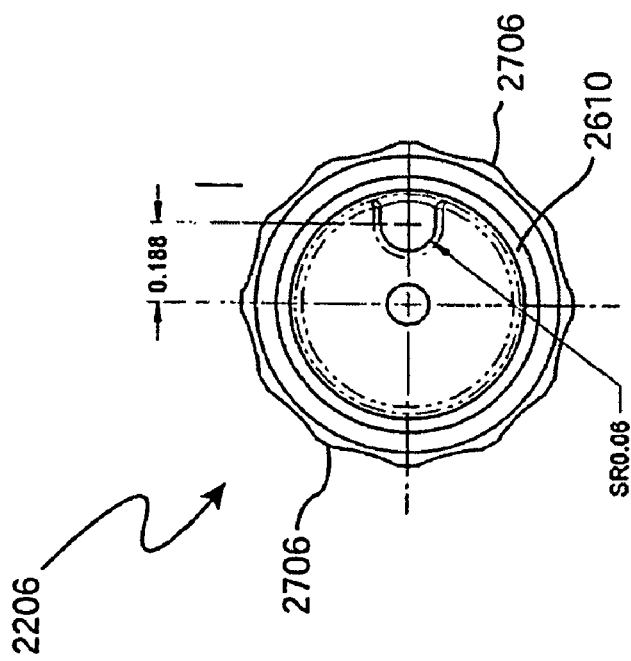
FIG. 28 is a top view of an embodiment of a second piece of a two-piece collection container attachment fitting of FIG. 24.
Figure 30:
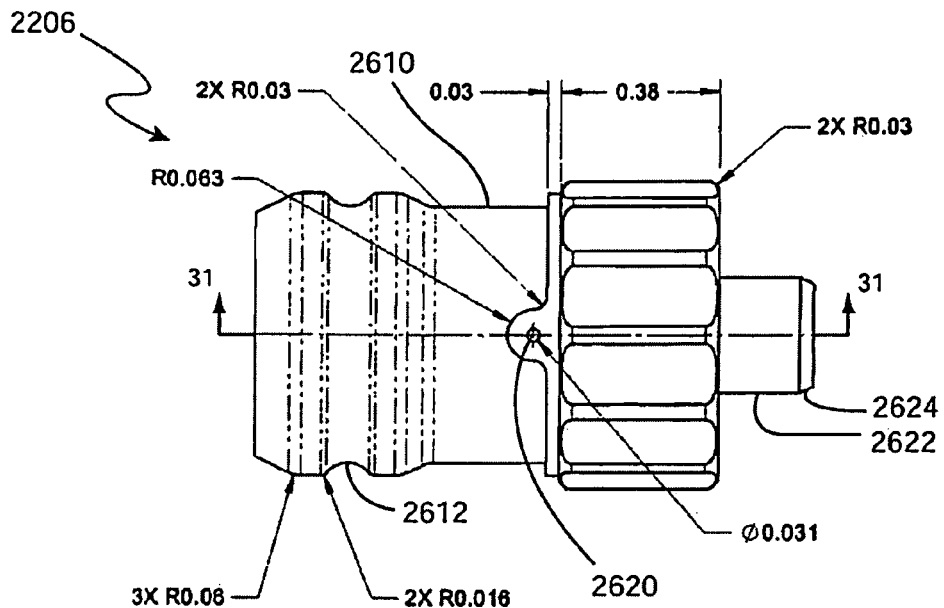
FIG. 30 is a side view of the embodiment of a second piece of a two-piece collection container attachment fitting of FIG. 24.
Figure 31:
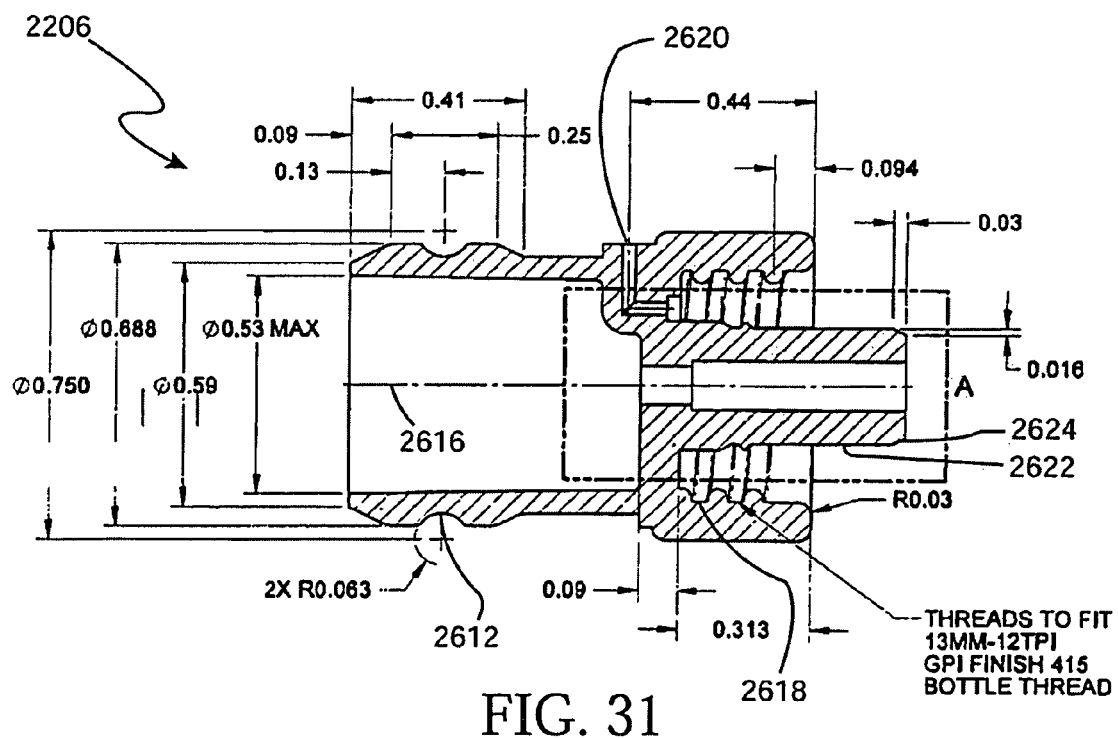
FIG. 31 is a cross-section view through line 31-31 of FIG. 30.
Figure 32:
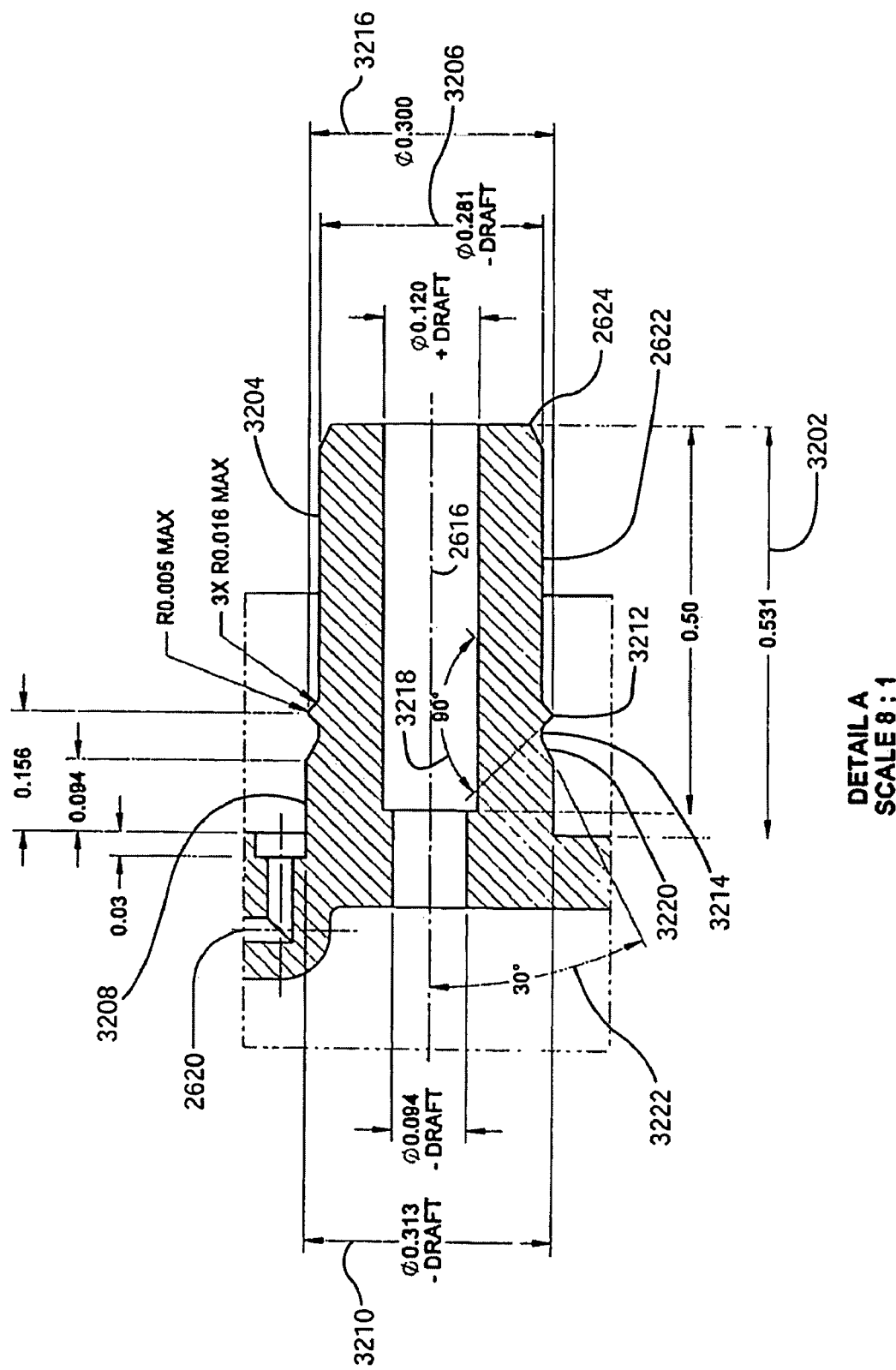
FIG. 32 is an enlarged view of section A of FIG. 31.

Referring to FIGS. 26 and 27, the second piece 2206 of the two-piece collection container attachment fitting includes bladder attachment portion 2610 arranged to accept an open end 2304 of the bladder 2202. In one embodiment, the bladder attachment portion 2610 is cylindrical and includes a radial groove 2612 on an exterior surface. The radial groove 2612 is sized to seat an elastic rings 2210. In one embodiment, the radial groove 2612 has a generally semi-circular cross section. The bladder attachment portion 2610 is inserted into an open end 2304 of the bladder 2202, opposite the other open end 2304 attached to the bladder attachment portion 2404 of the first piece 2204, a sufficient distance so that the open end 2304 extends past the radial groove 2612. An elastic ring 2210 is seated in the radial groove 2612 to seal the bladder 2202 between the elastic ring 2210 and the bladder attachment portion 2610.

Referring to FIGS. 26-32, the second piece 2206 also includes a collection container attachment portion 2614, coaxially extending from the bladder attachment portion 2610. As illustrated, the collection container attachment portion 2614 is a multi-purpose fitting that is arranged for attachment to a collection bag 112 or a collection vial 2208. The collection device attachment portion 2614 includes an internally thread collar 2618 arranged to accept the corresponding threads of a collection vial 2208. A plurality of external nubs 2706 is provided to connect the threaded collar 2618 to a collection vial 2208. In one embodiment, the threaded collar 2618 does not spin free of the bladder attachment portion 2610. Disposed within the threaded collar 2618 is a vent 2620 that extends to an exterior surface of the collection container attachment portion 2614. An extension tube 2704 ensures that the "fresh" breath sample arrives at the bottom of vial 2208, thus flushing out any "old" air in the vial 2208 through vent 2620. The vent 2620 also prevents a suction vacuum from being created when the collection vial 2208 is removed.

The collection device attachment portion 2614 also includes a central cylindrical post 2622. The central cylindrical post 2622 is coaxial with the bladder attachment portion 2610. In one embodiment, the central post 2622 includes a coaxial central extension 2704 that extends a distance into the collection vial 2208. The central post 2622 press fits within the fill port 108 of a collection bag 112 and retained in that position by friction. A beveled or chamfered leading edge 2624 is provided to guide insertion of the post 2622 into the fill port 108. In one embodiment, the central post 2622 includes a first portion 3204 having a first diameter 3206 and a second portion 3208 having a second diameter 3210. The second diameter 3210 preferably is greater than the first diameter 3206. In one embodiment, central post 2622 has an annular ridge 3212 with a cross sectional angle 3218 that is about 90°, and an annular groove 3214 with an inclined face 3220 leading to the second portion 3208 that forms an angle 3222 of about 30° with the central axis 2616 of the second portion 3208. In one embodiment, the central post 2622 has an overall length 3202 of about 0.5 inches. When the collection container attachment portion 2614 is engaged with a collection vial 2208, the central cylindrical post 2622 directs breath samples into the vial 2208.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singularly or in combination with other embodiment(s) and steps or elements from methods in accordance with the present invention can be executed or performed in any suitable order. Therefore, it will be understood that the appended claims are intended to cover all such modifications and embodiments, which would come within the spirit and scope of the present invention.

What is claimed is:

1. A breath collection apparatus for sampling air from a patient, comprising:
    a face mask for covering said patient's mouth and nose;
    a valve assembly in fluid communication with said face mask, said valve assembly comprising a housing having an inlet in fluid communication with said face mask, an outlet conduit, and a valve body forming an enclosure between said inlet and outlet conduit, said valve body being defined by an annular shoulder connected to said inlet by a flared wall, an annular flange surrounding said outlet conduit and engaged to the annular shoulder, a plurality of distinct holes disposed radially around said outlet conduit, and a flexible valve seated in said housing, said flexible valve comprising a unitary elastomeric member having a central duckbill portion extending into said outlet conduit to a one-way exhalation passage, and an umbrella diaphragm portion attached to and surrounding said central duckbill portion, said flexible valve being seated inside said valve body with said umbrella diaphragm resting against said flange and covering said plurality of distinct holes disposed radially around said outlet conduit to define a one-way inhalation passage;
    a collection container attachment assembly in fluid communication with said outlet conduit;

a collection container attached to said collection container attachment assembly and in fluid communication with the outlet conduit of said valve assembly for storing a patient's exhaled breath.

2. The breath collection apparatus for sampling air from a patient according to claim 1, wherein said collection container attachment assembly further comprises a multipurpose attachment fitting including a tubular post for attachment to a collection bag and a threaded collar for attachment to a collection vial.

3. The breath collection apparatus for sampling air from a patient according to claim 2, wherein said collection container attachment assembly further comprises a vent located so that when said collar is engaged with a collection vial, non-sample air can be flushed out of said collection vial as sample air flows into said collection vial.

4. The breath collection apparatus for sampling air from a patient according to claim 1, further comprising a bladder interconnected between said collection container attachment assembly and outlet conduit for intermediate collection of breath.

5. The breath collection apparatus of claim 4, wherein said bladder comprises a flexible film.

6. A breath collection apparatus for sampling air from the lungs of patients, comprising:
- a face mask for covering a patient's mouth and nose;
- a valve assembly comprising a tubular inlet connected to said face mask, a tubular outlet, an enlarged valve housing connecting said tubular inlet and said tubular outlet and having an annular shoulder connected to said inlet by a flared wall, an annular flange surrounding said outlet conduit and engaged to the annular shoulder, and a plurality of distinct holes disposed radially around said outlet conduit, and a flexible valve member seated in said housing said flexible valve comprising a unitary elastomeric member seated in said valve housing including an umbrella diaphragm portion resting against said flange and covering said plurality of distinct holes to allow one-way inhalation, and a duckbill portion joined integrally to said diaphragm portion and extending axially there from into said tubular outlet for one-way exhalation;
- a collection bag attachment fitting including a tubular post; and
- a collection bag attached to said tubular post for storing a patient's exhaled breath.

7. The breath collection apparatus of claim 6, wherein said collection container attachment fitting comprises:
- a tubular valve attachment portion for cooperative sealed fluid engagement with said valve assembly, defining a central cavity; and
- a tubular post protruding from said tubular valve attachment portion for insertion into a fill port of a collection bag, having a central bore in fluid communication with said central cavity.

8. The breath collection apparatus of claim 7, wherein said tubular post further comprises an annular ridge and an annular groove adjacent to said annular ridge around the outer periphery of said tubular post for locking engagement with a fill port of a collection bag.

9. The breath collection apparatus of claim 6, wherein said collection container attachment fitting further comprises:
- a collar extending from said valve attachment portion, comprising:
  - threads on an interior surface of said collar for cooperative engagement with corresponding threads on a collection vial; and
  - a vent located so that when said collar is engaged with a collection vial, non-sample air can be flushed out of said collection vial as sample air flows into said collection vial.

10. The breath collection apparatus of claim 9, wherein said collar is concentric with said tubular post.

11. The breath collection apparatus of claim 10, wherein said tubular post further comprises a tube that extends into the bottom of an engaged collection vial for ensuring that a patient's breath arrives at the bottom of said collection vial.

* * * * *